(12) United States Patent
Blank et al.

(10) Patent No.: US 7,888,068 B2
(45) Date of Patent: Feb. 15, 2011

(54) CLONING OF HONEY BEE ALLERGEN C

(75) Inventors: Simon Blank, Hamburg (DE);
Benjamin Bockisch, Frankfurt am Main (DE); Thomas Grunwald, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 298 days.

(21) Appl. No.: 11/823,075

(22) Filed: Jun. 26, 2007

(65) Prior Publication Data
US 2008/0317669 A1 Dec. 25, 2008

(30) Foreign Application Priority Data
Jun. 26, 2006 (EP) .................................. 06013165

(51) Int. Cl.
C12N 15/09 (2006.01)
C12N 1/20 (2006.01)
C12N 15/00 (2006.01)
C12N 5/00 (2006.01)
C12N 5/02 (2006.01)
C07H 21/02 (2006.01)
C07H 21/04 (2006.01)

(52) U.S. Cl. ................ 435/69.3; 435/252.3; 435/320.1; 435/325; 435/455; 536/23.1; 536/23.5

(58) Field of Classification Search .................. None
See application file for complete search history.

(56) References Cited

U.S. PATENT DOCUMENTS 6,551,795 B1 * 4/2003 Rubenfield et al. ......... 435/69.1

FOREIGN PATENT DOCUMENTS

WO WO 01/88085 A2 2/2001

OTHER PUBLICATIONS

Metzler et all 'Solution structure of human CTLA-4 and delineation of a CD80/CD86 binding site conserved in CD28. Nature Structural Biol. 4:527-531, 1997.*
Bork et al. 'Powers and Pitfalls in Sequence Analysis: The 70% Hurdle.' Genome Research. 10:398-400, 2000.*
Doerks et al. 'Protein annotation: detective work for function prediction.' Trends in Genetics. 14:248-250, 1998.*
Smith et al. The challenges of genome sequence annotation or "the devil is in the details". Nat. Biotech.15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Lerner et al. 'Tapping the immunological repertoire to produce antibodies of predetermined specificity.' Nature. 299:593-596, 1982.*
Altschul SF, Gish W, Miller W, Myers EW, Lipman DJ. (1990) Basic local alignment search tool. J. Mol. Biol., 215(3): 403-10.

Barbee RA, Lebowitz MD, Thompson HC, Burrows B. (1976) Immediate skin-test reactivity in a general population sample. Ann. Intern. Med., 84(2): 129-33.
Borovkov AY, Rivkin MI. (1997) XcmI-containing vector for direct cloning of PCR products. Biotechniques, 22(5): 812-14.
Castro FF, Palma MS, Brochetto-Braga MR, Malaspina O, Lazaretti J, Baldo MA, Antila MA, Zuppi LJ, Croce J, Cossermelli W. (1994) Biochemical properties and study of antigenic cross-reactivity between Africanized honey bee and wasp venom. J. Investig. Allergol. Clin. Immunol., 4(1): 37-41.
Dobers J, Zimmermann-Kordmann M, Leddermann M, Schewe T, Reutter W, Fan H. (2002) Expression, purification, and characterization of human dipeptidyl peptidase IV/CD26 in Sf9 insect cells. Protein Expr. Purif.; 25(3):527-32.
Dotimas EM and Hider RC. (1987) Honeybee venom. Bee World, 68(2): 51-71.
Eich-Wanger C, Müller UR. (1998) Bee sting allergy in beekeepers. Clin. Exp. Allergy, 28(10): 1292-98.
Elbein AD. (1991) The role of N-linked oligosaccharides in glycoprotein function. Trends Bioctechnol., 9(10): 346-52.
Gmachl M, Kreil G. (1993) Bee venom hyaluronidase is homologous to a membrane protein of mammalian sperm. Proc. Natl. Acad. Sci. USA, 90(8): 3569-73.
Grunwald T, Bockisch B, Spillner E, Ring J, Bredehorst R, Ollert MW. (2006) Molecular cloning and expression in insect cells of honeybee venom allergen acid phosphatase (Api m 3). J. Allergy Clin. Immunol., 117(4): 848-54.
Habermann E. (1974) Bienen- and Wespenstiche aus medizinscher Sicht. Allgemeinc Deutsche Imkerzeitung, 11: 301-04.
Hamilton RG. (2002) Diagnosis of Hymenoptera venom sensitivity. Curr. Opin. Allergy Clin. Immunol., 2(4): 347-51.
Helbling A, Hurni T, Mueller UR, Pichler WJ. (2004) Incidence of anaphylaxis with circulatory symptoms: a study over a 3-year period comprising 940,000 inhabitants of the Swiss Canton Bern. Clin. Exp. Allergy, 34(2): 285-90.
Hemmer W, Focke M, Kolarich D, Dalik I, Götz M, Jarisch R. (2004) Identification by immunoblot of venom glycoproteins displaying immunoglobulin E-binding N-glycans as cross-reactive allergens in honeybee and yellow jacket venom. Clin. Exp. Allergy, 34(3): 460-69.
Hoffman DR. Hymenoptera venom proteins in Natural Toxins 2: Structure, Mechanism of Action, and Detection, in *Advances in Experimental Medicine and Biology* (Singh BR and Tu AT, Eds., Plenum Press, NY, 1996).
Hoffman DR, Dove DE, Moffitt JE, Stafford CT. (1988) Allergens in Hymenoptera venom. XXI. Cross-reactivity and multiple reactivity between fire ant venom and bee and wasp venoms. J. Allergy Clin. Immunol., 82(5 Pt 1): 828-34.

(Continued)

*Primary Examiner* — Nora M Rooney
(74) *Attorney, Agent, or Firm* — Ballard Spahr LLP

(57) ABSTRACT

The present invention relates to a nucleic acid encoding a polypeptide capable of binding to IgE from subjects allergic to venom of an insect from the order *Hymenoptera* having a homology of more than 70% to the amino acid sequence of SEQ ID NO: 2, which is the honey bee allergen C (Api m 5). The invention further relates to expression vectors, host cells and polypeptides encoded by the nucleic acid, as well as diagnostic and pharmaceutical uses thereof.

16 Claims, 8 Drawing Sheets

OTHER PUBLICATIONS

Hoffman DR, Shipman WH. (1976) Allergens in bee venom. I. Separation and identification of the major allergens. J. Allergy Clin. Immunol., 58(5): 551-62.

Hoffman DR, Shipman WH, Babin D. (1977) Allergens in bee venom II. Two new high molecular weight allergenic specificities. J. Allergy Clin. Immunol., 59(2): 147-53.

Huby RD, Dearman RJ, Kimber I. (2000) Why are some proteins allergens? Toxicol. Sci., 55(2): 235-46.

Hunt KJ, Valentine MD, Sobotka AK, Benton AW, Amodio FJ, Lichtenstein LM. (1978) A controlled trial of immunotherapy in insect hypersensitivity. N. Engl. J. Med., 299(4): 157-61.

Jenkins N, Parekh RB, James DC. (1996) Getting the glycosylation right: implications for the biotechnology industry. Nat. Biotechnol., 14(8): 975-81.

Kettner A, Hughes GJ, Frutiger S, Astori M, Roggero M, Spertini F, Corradin G. (2001) Api m 6: a new bee venom allergen. J. Allergy Clin. Immunol., 107(5): 914-20.

Kettner A, Henry H, Hughes GJ, Corradin G, Spertini F. (1999) IgE and T-cell responses to high-molecular weight allergens from bee venom. Clin. Exp. Allergy, 29(3): 394-401.

King TP. (1990) Insect venom allergens. Monogr. Allergy, 28: 84-100.

Kuchler K, Gmachl M, Sippl MJ, Kreil G. (1989) Analysis of the cDNA for phospholipase A2 from honeybee venom glands. The deduced amino acid sequence reveals homology to the corresponding vertebrate enzymes. Eur. J. Biochem., 184(1): 249-54.

Kulike VH. (1986) Zur Struktur and Funktion des Hymenopterenstachels. Amts- and Mittellungsblatt der Bundesanstalkt für Materialprüfung (BAM), 16: 519-50.

Kumagai Y, Konishi K, Gomi T, Yagishita H, Yajima A, Yoshikawa M. (2000) Enzymatic properties of dipeptidyl aminopeptidase IV produced by the periodontal pathogen Porphyromonas gingivalis and its participation in virulence. Infect. Immun., 68(2): 716-24.

Müller UR. (2002) Recombinant Hymenoptera venom allergens. Allergy, 57(7): 570-76.

Müller UR. (2001) New developments in the diagnosis and treatment of hymenoptera venom allergy. Int. Arch. Allergy Immunol., 124(4): 447-53.

Obispo T. (2002) New concepts in the manufacture of Hymenoptera venom extracts. Alergol. Inmunol. Clin., 17: 215-20.

Petersen A, Mundt C.J. (2001) Investigations on the carbohydrate moieties of glycoprotein allergens. Chromatogr. B. Biomed. Sci. Appl., 756(1-2): 141-50.

Poulsen LK. (2001) In vivo and in vitro techniques to determine the biological activity of food allergens. J. Chromatogr. B. Biomed. Sci. Appl., 756(1-2): 41-55.

Schiavino D, Nucera E, Pollastrini E, De Pasquale T, Buonomo A, Bartolozzi F, Lombardo C, Roncallo C, Patriarca G. (2004) Specific ultrarush desensitization in Hymenoptera venom-allergic patients. Ann. Allergy Asthma Immunol., 92(4): 409-13.

Schmid-Grendelmeier P, Crameri R. (2001) Recombinant allergens for skin testing. Int. Arch. Allergy Immunol., 125(2): 96-111.

Sobotka A, Franklin R, Valentine M, Adkinson NF, Lichtenstein L. (1974) Honeybee venom: Phospholipase A as the major allergen. J. Clin. Allergy Clin. Immunol., 53(2): 103.

Sobotka AK, Franklin RM, Adkinson NF Jr, Valentine M, Baer H, Lichtenstein LM. (1976) Allergy to insect stings. II. Phospholipase A: the major allergen in honeybee venom. J. Allergy Clin. Immunol., (1): 29-40.

Sudowe S, Montermann E, Steitz J, Tüting T, Knop J, Reske-Kunz AB. (2002) Efficacy of recombinant adenovirus as vector for allergen gene therapy in a mouse model of type I allergy. Gene Ther., 9(2): 147-56.

Tretter V, Altmann F, Kubelka V, März L, Becker WM. (1993) Fucose alpha 1,3-linked to the core region of glycoprotein N-glycans creates an important epitope for IgE from honeybee venom allergic individuals. Int. Arch. Allergy Immunol., 102(3): 259-66.

Vlasak R, Unger-Ullmann C, Kreil G, Frischauf AM. (1983) Nucleotide sequence of cloned cDNA coding for honeybee prepromelittin. Eur. J. Biochem., 135(1): 123-26.

Williams LW, Bock SA. (1999) Skin testing and food challenges in allergy and immunology practice. Clin. Rev. Allergy Immunol., 17(3): 323-38.

Wood CL, Hoffman DR. (1983) Two-dimensional polyacrylamide gel electrophoresis of hymenoptera venom and venom sac extracts. Toxicon., 21(2): 291-99.

Wypych JI, Abeyounis CJ, Reisman RE. (1989) Analysis of differing patterns of cross-reactivity of honeybee and yellow jacket venom-specific IgE: use of purified venom fractions. Int. Arch. Allergy Appl. Immunol., 89(1): 60-6.

Hoffman, D., Hymenoptera Venom Allergens, (2006) Clin. Rev. in Allergy & Immun., vol. 30: 109-128.

* cited by examiner

Figure 6

```
   1    ATG GAG GTA CTG GTG CAG CTG GCG CTG CTG CTG GTG GTG CAC GGA
  46    TCG CTG GTC GTC CTC GTT GCT GGA AAA TCC GTT CCA CGA GTG ATC
  91    GAC CAG GAC TTG GAG AGA TAC GAG CCC CTC GAA GAG GAG GAT CAT
 136    CGG GGT GCA AGG GTC CCT TTC AAC CTG GAG GAG ACT TAC GAT CAA
 181    AGT TTC CGG GCG AAC AGT TTC AAC GGC ACC TGG AAA ACG GAC AGG
 226    GAA ATC CTT TAC TCG GAC AAC TAC GTC GGC GAT ATC CGA TTG TTC
 271    GAC GTC ACG ACA GGA TCG GGC ACC GTT CTC CTC GAT TCG TCC GTC
 316    ACG GCC GAT TTC GAC AAA GCG TCC GTG ATG TTT TCC TTC GAC AAT
 361    TCC CAC GTA GCT ATC GGC CAC GAC TAC GTG AAC GGG TTT CGA TAC
 406    TCG ATA CAC CAA AAG TGC ACC GTG TAC AAC ATT AAA TCC AGA ACG
 451    TTC ACG GAT ATC GCG AAT GGC GAT CGC ATA CCA CTG TTC AAA TGG
 496    TCG CCC ACG AGG AAC GCT TTG ATT TAC GTT CAC AAG AAC GAT ATC
 541    TAT TAT CAG GTG TTC TTC GAG GGT GGC AGC GAC ACT CGA AGG ATA
 586    ACG AAC ACC GGC GTC CCG GAC ATC GTT TTC AAC GGG ATA CCC GAC
 631    TGG GTT TAC GAG GAG GAA GTG CTG GGC TCC CCG GTC GCA TTC TGG
 676    ATC TCG CCC GAC GGA CGA CAC CTT GCT TTC GCC ACG TTC AAC GAC
 721    ACC AAC GTC CGC GAT ATC GTG ATA TCT AAA TAC GGC TCC CCT GGA
 766    AAC TCG AGG GAT CAA TAT CCG AAC GAG ATC AGG ATA AAA TAT CCG
 811    AAA GCG GGC ACC ACG AAC CCA TTC GTG TCC CTG AGC GTG ATC GAC
 856    TTG CAC GAT CCC TCC TCG AAA TTG ATC GAT CTT CCG CCG CĆT GTC
 901    GAT GTC GTT GGA GCA GAC AAC GTT CTT TAT ACC GCG AAC TGG AGG
 946    AGG GAC GGC GAG ATT GTT GCG ACG TGG ACG AAC AGG GTG CAG AAC
 991    AAG GCC CAA TTA GTG CTG TAC GAC ACG AAG GGT AAC GCG AAT AAT
1036    ATT TAT TAC GAG GAG GAG ACC GAG GGT TGG CTT CGC ATC CAA CCA
1081    CCC CTC TAT CAC GAC CGA TAC GTG ATC GTT GCG AAG CTT CAA GAC
1126    TCG GGC ACG AAG GCG GGA CGG TTT CTC CAC GCG ACG AGG CTC GAG
1171    TAC AGG AAC GGC GCC CTG GTC GAC GAG ACG GAT TTG ACG CCT GGA
1216    ACG TGC GAG GTT ATC TCC CTG TTG CTC GTC GAC CAC GCC AGG GCC
1261    AGG CTC TAT TAC TTG GGC ACC GAG CTC GGC AAA CCA TCC CAC AAG
1306    AAT CTC TAC TCC GTC CAA TTG AGC GGC AAC GAG CCG CCC GTT TGC
1351    CTG TCG TGC GAC GTC CTC ACC CCC GAG GGG AAT CGT TGC ACC TAC
1396    GCC TAC GCC TAC TTC TCG ACC AAC GGT TCT CAT TAC GCG TTG TAC
1441    TGC GCC GGC CCA GAC CCT GTC TTC ATC GCG ATA GTG AAC GCG AAT
1486    CAC AGG CAG ATC TCG ATT TGG GAG GAG AAC CGA TCC CTT AGA CGC
1531    AAG TTG GCC GCC CGT ACT CAG CCG ATT GTC AAG AAT TTC AAC GTG
1576    AAC GCG AAC GGG TAC ACG AAC AAG GTT AAG CTT TAC CTG CCG CCC
1621    GAC TTC GAC GAG ACG AAA AAG TAT CCT CTG CTG ATC ACC GTG TAC
1666    GCA GGG CCG AAC ACT ATC AGG ATT ACG GAG GAG GCT ACG TAC GGG
1711    TTC GAG TCG TAC ATA GTG ACG AAC AGG AGC GTA ATT TAT GGG CGC
1756    ATC GAC GGG CGT GGA TCG GCG TAC AAA GGG AGC AAG ATG CTG TTC
1801    GAG ATC TAT CGC CGA CTC GGC ACC GTG GAG ATC GAG GAT CAG ATT
1846    ATT ATC ACC AGA ACG CTG CAG GAG AAG TAC TCG TGG ATC GAT TCG
1891    AAC AGG ACG GGC ATA TGG GGT TGG AGT TAC GGC GGT TTC TCG GCC
1936    GCC ATG GTG CTG GCC ACC GAC GCC GAG TCG GTG TTC AAG TGC GGC
1981    ATA TCA GTC GCA CCC GTC ACC TCC TGG ATT TAT TAC GAT TCC TTG
2026    TAC ACG GAA CGG TTC ATG GGC CTG CCG ACC CCG GAG GAC AAT CAG
2071    AGC GGT TAC AAC GAC ACG GAC GTG AGC AGG AGG GTG GAG GGT ATG
2116    CGA GGG AAA AAG TAC ATG CTG ATA CAC GGG ACA GCG GAC GAC AAC
2161    GTG CAC TAC CAG CAA ACC ATG ATG CTG AAC AAG GCT TTG GTG AAC
2206    AGC GAC ATA ATG TTC CAG CAG CAG ACG TAC ACG GAC GAG GCG CAC
2251    GCC CTC GGG AAC GTC TTC CCC CAT CTC TAC CAC ACC ACG GAC CGA
2296    TTC TGG GCC AAT TGT CTG GGA TAC TCC CAC TGA
```

Figure 7

```
  1   MEVLVQLALL  LVVHGSLVVL  VAGKSVPRVI  DQDLERYEPL  EEEDHRGARV
 51   PFNLEETYDQ  SFRANSFNGT  WKTDREILYS  DNYVGDIRLF  DVTTGSGTVL
101   LDSSVTADFD  KASVMFSFDN  SHVAIGHDYV  NGFRYSIHQK  CTVYNIKSRT
151   FTDIANGDRI  PLFKWSPTRN  ALIYVHKNDI  YYQVFFEGGS  DTRRITNTGV
201   PDIVFNGIPD  WVYEEEVLGS  PVAFWISPDG  RHLAFATFND  TNVRDIVISK
251   YGSPGNSRDQ  YPNEIRIKYP  KAGTTNPFVS  LSVIDLHDPS  SKLIDLPPPV
301   DVVGADNVLY  TANWRRDGEI  VATWTNRVQN  KAQLVLYDTK  GNANNIYYEE
351   ETEGWLRIQP  PLYHDRYVIV  AKLQDSGTKA  GRFLHATRLE  YRNGALVDET
401   DLTPGTCEVI  SLLLVDHARA  RLYYLGTELG  KPSHKNLYSV  QLSGNEPPVC
451   LSCDVLTPEG  NRCTYAYAYF  STNGSHYALY  CAGPDPVFIA  IVNANHRQIS
501   IWEENRSLRR  KLAARTQPIV  KNFNVNANGY  TNKVKLYLPP  DFDETKKYPL
551   LITVYAGPNT  IRITEEATYG  FESYIVTNRS  VIYGRIDGRG  SAYKGSKMLF
601   EIYRRLGTVE  IEDQIIITRT  LQEKYSWIDS  NRTGIWGWSY  GGFSAAMVLA
651   TDAESVFKCG  ISVAPVTSWI  YYDSLYTERF  MGLPTPEDNQ  SGYNDTDVSR
701   RVEGMRGKKY  MLIHGTADDN  VHYQQTMMLN  KALVNSDIMF  QQQTYTDEAH
751   ALGNVFPHLY  HTTDRFWANC  LGYSH*
```

Figure 8

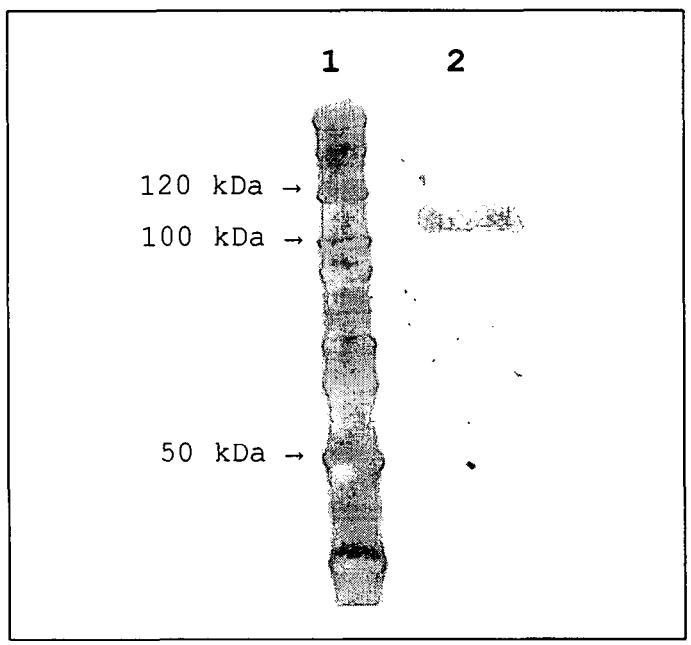

Figure 9

```
Human DPPIV      ---------MKTPWKVLLGLLGAAALVTIITVPVVLLNKGTDDATADSRKTYTLTDYLKN  51
Snake Gbb-IVa    ---------MKTVVKCLLGLLALGVIITAIVVPVVLLTR--DDS--DIRRKFSLEDYLSD  47
Bee   Api m 5    MEVLVQLALLLVVHGSLVVLVAGKSVPRVIDQDLERYEPLEEEDHRGARVPFNLEETYDQ  60

Human DPPIV      TYRLKLYSLRWISDHEYLYKQ--ENNILVFNAEYGNSSVFLENSTFDEFGHSINDYSISP 109
Snake Gbb-IVa    EFQYKSYNLRWMSGHEYVYTN--QNNVLLYNIDDERESIVLSNDTLDSFNSSQ--AILSP 103
Bee   Api m 5    SFRANSFNGTWKTDREILYSDNYVGDIRLFDVTTGSGTVLLDSSVTADFDKAS--VMFSF 118

Human DPPIV      DGQFILLEYNYVKQWRHSYTASYDIYDLNKRQLITEERIPNNTQWVTWSPVGHKLAYVWN 169
Snake Gbb-IVa    DRKFALLQYSYEKVWRHSYTASYHIYDLNNRTKITENPLPTNIQYISWSPVGHKLAYVYR 163
Bee   Api m 5    DNSHVAIGHDYVNGFRYSIHQKCTVYNIKSR-TFTDIANGDRIPLFKWSPTRNALIYVHK 177

Human DPPIV      NDIYVKIEPN--LPSYRITWTGKEDIIYNGITDWVYEEEVFSAYSALWWSPNGTFLAYAQ 227
Snake Gbb-IVa    NNVYVKATPN--ASPVQITENGAENKILNGLADWVYEEEMFGTHSALWWSPNGRFLAFAE 221
Bee   Api m 5    NDIYQVFFEGGSDTRRITNTGVPDIVFNGIPDWVYEEEVLGSPVAFWISPDGRHLAFAT 237

Human DPPIV      FNDTEVPLIEYSFYS---DESLQYPKTVRVPYPKAGAVNPTVKFFVVNTDSLSSVTNATS 284
Snake Gbb-IVa    INDTEVPVMEYSFYS---EDTLQYPKTIKIPYPKAGAINPTIRLFVLDIS----LSPKNI 274
Bee   Api m 5    FNDTNVRDIVISKYGSPGNSRDQYPNEIRIKYPKAGTTNPFVSLSVIDLHD----PSSKL 293

Human DPPIV      IQITAPASMLIGDHYLCDVTWATQERISLQWLRRIQNYSVMDICDYDESSGRWNCLVARQ 344
Snake Gbb-IVa    SEIVAPSSIISGDHYLSAVTWVTDERICVQWLRRIQNFSVLTICDY---SGAWHCPKERE 331
Bee              IDLPPPVDVVGADNVLYTANWRRDGEIVATWTNRVQNKAQLVLYDTKGNANNIYYEEETE 353

Human DPPIV      HIEMSTTGWVGRFRPSEPHFTLDGNSFYKIISNEEGYRHICYFQIDKKDCTFITKGTWEV 404
Snake Gbb-IVa    HLEESKTGWVGRFQPSEPYFTSDKISYYRIISDSEGYKHIHYTDSAGK-VKPITSGKWEV 390
Bee   Api m 5    GWLRIQPPLYHDRYVIVAKLQDSGTKAGRFLHATR----LEYRNGALVDETDLTPGTCEV 409

Human DPPIV      IGIEALTSD--YLYYISNEYKGMPGGRNLYKIQLSDYTKVTCLSCELNP---ERCQYYSV 459
Snake Gbb-IVa    ISISAVTNN--SLYFISNEFEGRPGGRHLYKVDLKNDLKKICITCNSKE---EACQYFSV 445
Bee   Api m 5    ISLLLVDHARARLYYLGTELG-KPSHKNLYSVQLSGNEPPVCLSCDVLTPEGNRCTYAYA 468

Human DPPIV      SFSKEAKYYQLRCSGPGLPLYTLHSSVNDKGLRVLEDNSALDKMLQNVQMPSKKLDFIIL 519
Snake Gbb-IVa    SFSTDSRYYKLNCYGPDLPYFTLQNSITDKAIKTLEDNNNLKNVLKEIQMPCKRLSNITL 505
Bee   Api m 5    YFSTNGSHYALYCAGPDPVFIAIVN-ANHRQISIWEENRSLRRKLAARTQPIVKNFNVNA 527

Human DPPIV      NETKFWYQMILPPHFDKSKKYPLLLDVYAGPCSQKADTVFRLNWATYLASTENIIVASFD 579
Snake Gbb-IVa    HGQTYWYQMILPPNFDESKKYPLLIDVYAGPCSQKADAAFRINWSTYLASSEGIIVASFD 565
Bee   Api m 5    NGYTNKVKLYLPPDFDETKKYPLLITVYAGPNTIRITEEATYGFESYIVTNRSVIYGRID 587

Human DPPIV      GRGSGYQGDKIMHAINRRLGTFEVEDQIEAARQFSKMG-FVDNKRIAIWGWSYGGYVTSM 638
Snake Gbb-IVa    GRGSGFQGDKILHAIYRRLGTYEVEDQISAAKLFSEMS-FVDKDRIAIWGWSYGGYVTSM 624
Bee   Api m 5    GRGSAYKGSKMLFEIYRRLGTVEIEDQIIITRTLQEKYSWIDSNRTGIWGWSYGGFSAAM 647

Human DPPIV      VLGSGSG-VFKCGIAVAPVSRWEYYDSVYTERYMGLPTPEDNLDHYRNSTVMSRAENFKQ 697
Snake Gbb-IVa    VLGAGSD-VFKCGIAVAPVSRWQYYDSIYTERYMGLPEKNDNLNFYENSTVMARAKNFRT 683
Bee   Api m 5    VLATDAESVFKCGISVAPVTSWIYYDSLYTERFMGLPTPEDNQSGYNDTVSRRVEGMRG 707

Human DPPIV      VEYLLIHGTADDNVHFQQSAQISKALVDVGVDFQAMWYTDEDHGIASSTAHQHIYTHMSH 757
Snake Gbb-IVa    VDYLLIHGTADDNVHFQQAAQISKALVDAEVDFQAMWYTDKDHGIGG-HAHSHIYQHMSH 742
Bee   Api m 5    KKYMLIHGTADDNVHYQQTMMLNKALVNSDIMFQQQTYTDEAHALGN--VFPHLYHTTDR 765

Human DPPIV      FIKQCFSLP- 766
Snake Gbb-IVa    FMKQCFKLP- 751
Bee   Api m 5    FWANCLGYSH 775
```

Figure 11

Comparison of exon structures of the two gene predictions

GeneMark.hmm prediction of NW_622532 (pos 1 thru 335000) (CORRECTNESS VERIFIED BY SEQUENCING)

| Exon | Type | Start pos | End pos | Start pos (gene) | End pos (gene) | Length (bp) | Intron Gap |
|---|---|---|---|---|---|---|---|
| 1 | Initial | 322941 | 322946 | 1 | 6 | 6 | |
| 2 | Internal | 324009 | 324078 | 7 | 76 | 70 | 1063 |
| 3 | Internal | 324594 | 324835 | 77 | 318 | 242 | 516 |
| 4 | Internal | 325502 | 325576 | 319 | 393 | 75 | 667 |
| 5 | Internal | 325648 | 325700 | 394 | 446 | 53 | 72 |
| 6 | Internal | 326006 | 326202 | 447 | 643 | 197 | 306 |
| 7 | Internal | 326320 | 326489 | 644 | 813 | 170 | 118 |
| 8 | Internal | 326759 | 326859 | 814 | 914 | 101 | 270 |
| 9 | Internal | 328102 | 328565 | 915 | 1378 | 464 | 1243 |
| 10 | Internal | 328638 | 328920 | 1379 | 1661 | 283 | 73 |
| 11 | Internal | 329126 | 329320 | 1662 | 1856 | 195 | 206 |
| 12 | Internal | 329388 | 329548 | 1857 | 2017 | 161 | 68 |
| 13 | Terminal | 329641 | 329951 | 2018 | 2328 | 311 | 93 |

Positions 327057 to 327839 are read as N in genomic data

GNOMON prediction of NW_622532 (pos 1 thru 335000), XM_393818 (WRONG)

| Exon | Type | Start pos | End pos | Start pos (gene) | End pos (gene) | Length (bp) | Intron Gap |
|---|---|---|---|---|---|---|---|
| 1 | Initial | 319231 | 319270 | 1 | 40 | 40 | |
| 2 | Internal | 324594 | 324835 | 41 | 282 | 242 | 5324 |
| 3 | Internal | 325502 | 325576 | 283 | 357 | 75 | 667 |
| 4 | Internal | 325648 | 325700 | 358 | 410 | 53 | 72 |
| 5 | Internal | 326006 | 326202 | 411 | 607 | 197 | 306 |
| 6 | Internal | 326320 | 326489 | 608 | 777 | 170 | 118 |
| 7 | Internal | 326759 | 326859 | 778 | 878 | 101 | 270 |
| 8 | Internal | 328102 | 328565 | 879 | 1342 | 464 | 1243 |
| 9 | Internal | 328638 | 328920 | 1343 | 1625 | 283 | 73 |
| 10 | Internal | 329126 | 329320 | 1626 | 1820 | 195 | 206 |
| 11 | Internal | 329388 | 329548 | 1821 | 1981 | 161 | 68 |
| 12 | Terminal | 329641 | 329951 | 1982 | 2292 | 311 | 93 |

Positions 327057 to 327839 are read as N in genomic data

SEQUENCE LISTING

```
<160> NUMBER OF SEQ ID NOS: 32

<210> SEQ ID NO 1
<211> LENGTH: 2328
<212> TYPE: DNA
<213> ORGANISM: Apis mellifera

<400> SEQUENCE: 1
atggaggtac tggtgcagct ggcgctgctg ctggtggtgc acggatcgct ggtcgtcctc      60
gttgctggaa aatccgttcc acgagtgatc gaccaggact tggagagata cgagcccctc     120
gaagaggagg atcatcgggg tgcaagggtc cctttcaacc tggaggagac ttacgatcaa     180
agtttccggg cgaacagttt caacggcacc tggaaaacgg acaggaaat cctttactcg      240 gacaactacg tcggcgatat ccgattgttc gacgtcacga caggatcggg caccgttctc     300
```

| | |
|---|---|
| ctcgattcgt ccgtcacggc cgatttcgac aaagcgtccg tgatgttttc cttcgacaat | 360 |
| tcccacgtag ctatcggcca cgactacgtg aacgggtttc gatactcgat acaccaaaag | 420 |
| tgcaccgtgt acaacattaa atccagaacg ttcacggata tcgcgaatgg cgatcgcata | 480 |
| ccactgttca aatggtcgcc cacgaggaac gctttgattt acgttcacaa gaacgatatc | 540 |
| tattatcagg tgttcttcga gggtggcagc gacactcgaa ggataacgaa caccggcgtc | 600 |
| ccggacatcg ttttcaacgg gatacccgac tgggtttacg aggaggaagt gctgggctcc | 660 |
| ccggtcgcat tctggatctc gcccgacgga cgacaccttg ctttcgccac gttcaacgac | 720 |
| accaacgtcc gcgatatcgt gatatctaaa tacggctccc ctggaaactc gagggatcaa | 780 |
| tatccgaacg agatcaggat aaaatatccg aaagcgggca ccacgaaccc attcgtgtcc | 840 |
| ctgagcgtga tcgacttgca cgatccctcc tcgaaattga tcgatcttcc gccgcctgtc | 900 |
| gatgtcgttg gagcagacaa cgttctttat accgcgaact ggaggaggga cggcgagatt | 960 |
| gttgcgacgt ggacgaacag ggtgcagaac aaggcccaat tagtgctgta cgacacgaag | 1020 |
| ggtaacgcga ataatattta ttacgaggag gagaccgagg gttggcttcg catccaacca | 1080 |
| cccctctatc acgaccgata cgtgatcgtt gcgaagcttc aagactcggg cacgaaggcg | 1140 |
| ggacggtttc tccacgcgac gaggctcgag tacaggaacg gcgccctggt cgacgagacg | 1200 |
| gatttgacgc tggaacgtg cgaggttatc tccctgttgc tcgtcgacca cgccagggcc | 1260 |
| aggctctatt acttgggcac cgagctcggc aaaccatccc acaagaatct ctactccgtc | 1320 |
| caattgagcg gcaacgagcc gcccgtttgc ctgtcgtgcg acgtcctcac ccccgagggg | 1380 |
| aatcgttgca cctacgccta cgcctacttc tcgaccaacg gttctcatta cgcgttgtac | 1440 |
| tgcgccggcc cagaccctgt cttcatcgcg atagtgaacg cgaatcacag gcagatctcg | 1500 |
| atttgggagg agaaccgatc ccttagacgc aagttggccg cccgtactca gccgattgtc | 1560 |
| aagaatttca cgtgaacgc gaacgggtac acgaacaagg ttaagcttta cctgccgccc | 1620 |
| gacttcgacg agacgaaaaa gtatcctctg ctgatcaccg tgtacgcagg gccgaacact | 1680 |
| atcaggatta cggaggaggc tacgtacggg ttcgagtcgt acatagtgac gaacaggagc | 1740 |
| gtaatttatg ggcgcatcga cgggcgtgga tcggcgtaca aagggagcaa gatgctgttc | 1800 |
| gagatctatc gccgactcgg caccgtggag atcgaggatc agattattat caccagaacg | 1860 |
| ctgcaggaga agtactcgtg gatcgattcg aacaggacgg gcatatgggg ttggagttac | 1920 |
| ggcggtttct cggccgccat ggtgctggcc accgacgccg agtcggtgtt caagtgcggc | 1980 |
| atatcagtcg cacccgtcac ctcctggatt tattacgatt ccttgtacac ggaacggttc | 2040 |
| atgggcctgc cgaccccgga ggacaatcag agcggttaca acgacacgga cgtgagcagg | 2100 |
| agggtggagg gtatgcgagg gaaaaagtac atgctgatac acgggacagc ggacgacaac | 2160 |
| gtgcactacc agcaaaccat gatgctgaac aaggctttgg tgaacagcga cataatgttc | 2220 |
| cagcagcaga cgtacacgga cgaggcgcac gccctcggga cgtcttccc ccatctctac | 2280 |
| cacaccacgg accgattctg ggccaattgt ctgggatact cccactga | 2328 |

<210> SEQ ID NO 2
<211> LENGTH: 775
<212> TYPE: PRT
<213> ORGANISM: Apis mellifera

<400> SEQUENCE: 2

Met Glu Val Leu Val Gln Leu Ala Leu Leu Leu Val Val His Gly Ser
1               5                   10                  15

Leu Val Val Leu Val Ala Gly Lys Ser Val Pro Arg Val Ile Asp Gln
            20                  25                  30

Asp Leu Glu Arg Tyr Glu Pro Leu Glu Glu Asp His Arg Gly Ala
        35                  40                  45

Arg Val Pro Phe Asn Leu Glu Glu Thr Tyr Asp Gln Ser Phe Arg Ala
        50                  55                  60

Asn Ser Phe Asn Gly Thr Trp Lys Thr Asp Arg Glu Ile Leu Tyr Ser
65                  70                  75                  80

Asp Asn Tyr Val Gly Asp Ile Arg Leu Phe Asp Val Thr Thr Gly Ser
                85                  90                  95

Gly Thr Val Leu Leu Asp Ser Ser Val Thr Ala Asp Phe Asp Lys Ala
            100                 105                 110

Ser Val Met Phe Ser Phe Asp Asn Ser His Val Ala Ile Gly His Asp
            115                 120                 125

Tyr Val Asn Gly Phe Arg Tyr Ser Ile His Gln Lys Cys Thr Val Tyr
    130                 135                 140

Asn Ile Lys Ser Arg Thr Phe Thr Asp Ile Ala Asn Gly Asp Arg Ile
145                 150                 155                 160

Pro Leu Phe Lys Trp Ser Pro Thr Arg Asn Ala Leu Ile Tyr Val His
                165                 170                 175

Lys Asn Asp Ile Tyr Tyr Gln Val Phe Phe Glu Gly Gly Ser Asp Thr
                180                 185                 190

Arg Arg Ile Thr Asn Thr Gly Val Pro Asp Ile Val Phe Asn Gly Ile
        195                 200                 205

Pro Asp Trp Val Tyr Glu Glu Glu Val Leu Gly Ser Pro Val Ala Phe
210                 215                 220

Trp Ile Ser Pro Asp Gly Arg His Leu Ala Phe Ala Thr Phe Asn Asp
225                 230                 235                 240

Thr Asn Val Arg Asp Ile Val Ile Ser Lys Tyr Gly Ser Pro Gly Asn
                245                 250                 255

Ser Arg Asp Gln Tyr Pro Asn Glu Ile Arg Ile Lys Tyr Pro Lys Ala
            260                 265                 270

Gly Thr Thr Asn Pro Phe Val Ser Leu Ser Val Ile Asp Leu His Asp
            275                 280                 285

Pro Ser Ser Lys Leu Ile Asp Leu Pro Pro Val Asp Val Val Gly
290                 295                 300

Ala Asp Asn Val Leu Tyr Thr Ala Asn Trp Arg Arg Asp Gly Glu Ile
305                 310                 315                 320

Val Ala Thr Trp Thr Asn Arg Val Gln Asn Lys Ala Gln Leu Val Leu
                325                 330                 335

Tyr Asp Thr Lys Gly Asn Ala Asn Asn Ile Tyr Glu Glu Glu Thr
            340                 345                 350

Glu Gly Trp Leu Arg Ile Gln Pro Pro Leu Tyr His Asp Arg Tyr Val
            355                 360                 365

Ile Val Ala Lys Leu Gln Asp Ser Gly Thr Lys Ala Gly Arg Phe Leu
    370                 375                 380

His Ala Thr Arg Leu Glu Tyr Arg Asn Gly Ala Leu Val Asp Glu Thr
385                 390                 395                 400

Asp Leu Thr Pro Gly Thr Cys Glu Val Ile Ser Leu Leu Val Asp
                405                 410                 415

His Ala Arg Ala Arg Leu Tyr Tyr Leu Gly Thr Glu Leu Gly Lys Pro
            420                 425                 430

Ser His Lys Asn Leu Tyr Ser Val Gln Leu Ser Gly Asn Glu Pro Pro

```
                435                 440                 445
Val Cys Leu Ser Cys Asp Val Leu Thr Pro Glu Gly Asn Arg Cys Thr
450                 455                 460
Tyr Ala Tyr Ala Tyr Phe Ser Thr Asn Gly Ser His Tyr Ala Leu Tyr
465                 470                 475                 480
Cys Ala Gly Pro Asp Pro Val Phe Ile Ala Ile Val Asn Ala Asn His
                485                 490                 495
Arg Gln Ile Ser Ile Trp Glu Glu Asn Arg Ser Leu Arg Arg Lys Leu
                500                 505                 510
Ala Ala Arg Thr Gln Pro Ile Val Lys Asn Phe Asn Val Asn Ala Asn
                515                 520                 525
Gly Tyr Thr Asn Lys Val Lys Leu Tyr Leu Pro Pro Asp Phe Asp Glu
                530                 535                 540
Thr Lys Lys Tyr Pro Leu Leu Ile Thr Val Tyr Ala Gly Pro Asn Thr
545                 550                 555                 560
Ile Arg Ile Thr Glu Glu Ala Thr Tyr Gly Phe Glu Ser Tyr Ile Val
                565                 570                 575
Thr Asn Arg Ser Val Ile Tyr Gly Arg Ile Asp Gly Arg Gly Ser Ala
                580                 585                 590
Tyr Lys Gly Ser Lys Met Leu Phe Glu Ile Tyr Arg Arg Leu Gly Thr
                595                 600                 605
Val Glu Ile Glu Asp Gln Ile Ile Ile Thr Arg Thr Leu Gln Glu Lys
610                 615                 620
Tyr Ser Trp Ile Asp Ser Asn Arg Thr Gly Ile Trp Gly Trp Ser Tyr
625                 630                 635                 640
Gly Gly Phe Ser Ala Ala Met Val Leu Ala Thr Asp Ala Glu Ser Val
                645                 650                 655
Phe Lys Cys Gly Ile Ser Val Ala Pro Val Thr Ser Trp Ile Tyr Tyr
                660                 665                 670
Asp Ser Leu Tyr Thr Glu Arg Phe Met Gly Leu Pro Thr Pro Glu Asp
                675                 680                 685
Asn Gln Ser Gly Tyr Asn Asp Thr Asp Val Ser Arg Arg Val Glu Gly
                690                 695                 700
Met Arg Gly Lys Lys Tyr Met Leu Ile His Gly Thr Ala Asp Asp Asn
705                 710                 715                 720
Val His Tyr Gln Gln Thr Met Met Leu Asn Lys Ala Leu Val Asn Ser
                725                 730                 735
Asp Ile Met Phe Gln Gln Gln Thr Tyr Thr Asp Glu Ala His Ala Leu
                740                 745                 750
Gly Asn Val Phe Pro His Leu Tyr His Thr Thr Asp Arg Phe Trp Ala
                755                 760                 765
Asn Cys Leu Gly Tyr Ser His
770                 775

<210> SEQ ID NO 3
<211> LENGTH: 10
<212> TYPE: PRT
<213> ORGANISM: Apis mellifera
<220> FEATURE:
<221> NAME/KEY: MISC_FEATURE
<222> LOCATION: (1)..(1)
<223> OTHER INFORMATION: Residue might be A or N
<220> FEATURE:
<221> NAME/KEY: MISC_FEATURE
<222> LOCATION: (4)..(4)
<223> OTHER INFORMATION: Residue might be P or N
<220> FEATURE:
```

```
<221> NAME/KEY: MISC_FEATURE
<222> LOCATION: (6)..(6)
<223> OTHER INFORMATION: Residue might be Y or N

<400> SEQUENCE: 3

Xaa Gln Leu Xaa Leu Xaa Asp Arg Asp Gln
1               5                   10

<210> SEQ ID NO 4
<211> LENGTH: 10
<212> TYPE: PRT
<213> ORGANISM: Apis mellifera
<220> FEATURE:
<221> NAME/KEY: MISC_FEATURE
<222> LOCATION: (2)..(4)
<223> OTHER INFORMATION: Residues could not be determined

<400> SEQUENCE: 4

Ala Xaa Xaa Xaa Asn Pro Phe Val Ser Leu
1               5                   10

<210> SEQ ID NO 5
<211> LENGTH: 14
<212> TYPE: PRT
<213> ORGANISM: Apis mellifera

<400> SEQUENCE: 5

Val Pro Phe Asn Leu Glu Glu Thr Tyr Asp Gln Ser Phe Arg
1               5                   10

<210> SEQ ID NO 6
<211> LENGTH: 13
<212> TYPE: PRT
<213> ORGANISM: Apis mellifera

<400> SEQUENCE: 6

Glu Ile Leu Tyr Ser Asp Asn Tyr Val Gly Asp Ile Arg
1               5                   10

<210> SEQ ID NO 7
<211> LENGTH: 16
<212> TYPE: PRT
<213> ORGANISM: Apis mellifera

<400> SEQUENCE: 7

Asn Asp Ile Tyr Tyr Gln Val Phe Phe Glu Gly Gly Ser Asp Thr Arg
1               5                   10                  15

<210> SEQ ID NO 8
<211> LENGTH: 14
<212> TYPE: PRT
<213> ORGANISM: Apis mellifera

<400> SEQUENCE: 8

Leu Gly Thr Val Glu Ile Glu Asp Gln Ile Ile Ile Thr Arg
1               5                   10

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 9
tttttttttt tttttttttt                                              20
```

<210> SEQ ID NO 10
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 10
aaccgcggtt atcagtggga gtatcccaga ca                          32

<210> SEQ ID NO 11
<211> LENGTH: 57
<212> TYPE: DNA
<213> ORGANISM: Artificial Sequence
<220> FEATURE:
<223> OTHER INFORMATION: Oligonucleotide Primer

<400> SEQUENCE: 11
gaaaaagtat cctctgctga tcaacgtgta cgcagggccg aacactatca ggattac    57

<210> SEQ ID NO 12
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 12
gcctcctccg taatcctgat agtgttcggc cc                          32

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 13
cgggcaccac gaacccattc gtgtccctga gcg                         33

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 14
agaacgttgt ctgctccaac g                                      21

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 15
atggccatct ggtgggaatt atttcgcatt cga                         33

<210> SEQ ID NO 16
<211> LENGTH: 33
<212> TYPE: DNA
<213> ORGANISM: Artificial Sequence
<220> FEATURE:

```
<223> OTHER INFORMATION: Oligonucleotide Primer

<400> SEQUENCE: 16
atggaggtac tggtgcagct ggcgctgctg ctg                                    33

<210> SEQ ID NO 17
<211> LENGTH: 32
<212> TYPE: DNA
<213> ORGANISM: Artificial Sequence
<220> FEATURE:
<223> OTHER INFORMATION: Oligonucleotide Primer

<400> SEQUENCE: 17
gatctctaga aaatccgttc cacgagtgat cg                                     32

<210> SEQ ID NO 18
<211> LENGTH: 44
<212> TYPE: DNA
<213> ORGANISM: Artificial Sequence
<220> FEATURE:
<223> OTHER INFORMATION: Oligonucleotide Primer

<400> SEQUENCE: 18
gatcgcggcc gcgcctcctc cgtaatcctg atagtgttcg gccc                        44

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 19
gtaaaacgac ggccagtgcc aa                                                22

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 20
caggaaacag ctatgaccat ga                                                22

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 21
cgcaacgatc tggtaaacac                                                   20

<210> SEQ ID NO 22
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 22
gacaatacaa actaagattt agtcag                                            26
```

<210> SEQ ID NO 23
<211> LENGTH: 9000
<212> TYPE: DNA
<213> ORGANISM: Apis mellifera
<220> FEATURE:
<221> NAME/KEY: misc_feature
<222> LOCATION: (5058)..(5839)
<223> OTHER INFORMATION: n is a, c, g, or t

<400> SEQUENCE: 23

| | |
|---|---|
| tcttgtataa ttcttaaatt cgaagttgga agggagatta ggagcaggag taaaattatt | 60 |
| cttgtataat tcttaaattc gaagggagat taggaggagg aataaaatta ttcttgtata | 120 |
| attcttaaat tcgaaattgg aagggagatt aggaggagga ataagaaaat tagtttggaa | 180 |
| tggaagattt ttttttcttt agagaaaggg ttttttggaaa gttgaagttg ttgagagttg | 240 |
| tttgtcaatg tagatagata tttggaagag agattaggag gaggaataag aaaatttgtt | 300 |
| tggaatggaa gattttttc tcttagagaa agagttttg gaaagttgaa gttgtttgtc | 360 |
| gatttgtaag aaagcgatag atatctattt atttttatcg ttatcgttcc gagagataat | 420 |
| tgtaaatgtg tatgtatcat actcatcgat aaattagttg ttacaaagat ctgtttactc | 480 |
| gtttttagtt cgttttcttt cgagtctcgt gacacgtgac agcaatttta tctctcgttt | 540 |
| cgagcagaga cgatgttcaa aacgtgacgt tattcgcgtt tagccgcgca ataatcgttg | 600 |
| ctctcttttt ttcgtcttca tcgagacgag taatcggagg atgacgttta atccgacttc | 660 |
| ggatccggat attttaattt tcacggagtt ccggaccgg ttcatcaagt ggatcatttg | 720 |
| acgcgaccga tccgatcgaa tatttctccg atccacggat atgtcgcttc ccgatttcga | 780 |
| aacgtgaaaa tatatatata catcacgaga tcgtgagaga gaaactaagc gcaggaattc | 840 |
| gatgagccag cgtggaagtg ttttcatcg aaaagcgttc ttcgagggga acccaggaaa | 900 |
| agtgttttc gtctcgtggc tggagagaag gcaacgaaaa gatggaggtt aacttgtaaa | 960 |
| atgtacaatt cgatcgtgtt gaataataga atattatttt ctttttttc gaacctgatt | 1020 |
| aaatattaac gcatttcgtc gattcggata ttggatcacg aagaattcat ttgaattaaa | 1080 |
| actcgactcg agtaagaaaa tacgagtttg tttaatttca agccagccgt tctccctcct | 1140 |
| ttttcattaa gagaaactcg ccgaaagatt ggagcacgtg cggataacgt tttctattct | 1200 |
| attttttaaa cgttttttat tttttttgaa aattctttat caccgtaaaa atttcaaacg | 1260 |
| tgtctttcga aacttttaaa ctttttatcg cgacagtaac gatcgggcat taaacgggga | 1320 |
| attcgagtga acatttaact tctgactcga gcctcttcga agaaaatcgt aacatctccg | 1380 |
| atctaaataa taaactcgag ttttaacaa ggatcgatta ttattcgagg catcgatcct | 1440 |
| atcccttgaa tgattcgcaa caacagtcga agactttcga cttttgcgc gcaagtcgac | 1500 |
| gattatctc gccagcaacc agtctctcga ccggttcttc cttccttctt ttatacaatt | 1560 |
| taaccagttt ccaattcgcg ataacgttgg ataaacggga tcatccttgg cgactatcga | 1620 |
| ctcctcgagt ttaaatttac ggatatcgta gaatatcgaa acgagagaag aagtggataa | 1680 |
| gaaagttata tcttcaataa gaaatacaac cattgtatta aacaatcact ttcttttaa | 1740 |
| attttactcg ttcgaagaca aatttctttt cattctctcg aatcatcttc aatcacttt | 1800 |
| ctcttcaatg aatttaaaaa taggagaatc atcgaataat cgttgagacg attctgcact | 1860 |
| ttcgtttctc tctttctctc ctccatttct cccttcttcg acaagatgcc acgaggaaga | 1920 |
| ggaccttaga aaggattctc cttttttatat ctatatatat atttgtatat tttttcttct | 1980 |
| ccaactgaag ggagtgaaac gtttcgcagg tactggtgca gctggcgctg ctgctggtgg | 2040 |

-continued

```
tgcacggatc gctggtcgtc ctcgttgctg gaaaatccgg tgagtcttcc gcttctttgt    2100
ccccgagaga taatcgcgct gagccgctta gggaccggat gcctcgagac gcgtccggat    2160
gcctcgccga ttcgcctcga gataatcgcg aggatatcgt tttccttaaa cttctcctcc    2220
tcgctttgag gagagaaaaa aatttgaatt aatccagaaa caccgtttga ctttgagatt    2280
tacaaattat tacgtactta taaatactac cataaattat atatactttc gatgataaat    2340
tattctcgca atacctgaat gtaaacattg gttggaagcg tgtaacaacg taatacagat    2400
cgagtcacca cgttattgac ccagttacgg cttaacgaat aataaactaa attaatcagt    2460
cctcgtctat cgcgagagaa tcgacggggt tcagacgta ctttgaacaa ttattattcc     2520
atttgcctcg atacgaagtg ctcgatttct tcctccatgt ttattcgaaa cgagagagt     2580 cttcttctat tcagttccac gagtgatcga ccaggacttg gagagatacg agcccctcga    2640
agaggaggat catcggagtg caagggtccc tttcaacctg gaggagactt acgatcaaag    2700
tttccgggcg aacagtttca acggcacctg gaaaacggac agggaaatcc tttactcgga    2760
caactacgtc ggcgatatcc gattgttcga cgtcacgaca ggatcgggca ccgttctcct    2820
cgattcgtcc gtcacggtga gccttcatcg caattttgca aattattgta gcagatttc     2880 gaaattgaag aaacgatttt ctcttcgttg gggcgcgata aatttcaatc tcgagaacaa    2940
accgctggga acgtcctgcg ggaggcaaac aacggtttga ttaatcggca cggaaattct    3000
ctccgtccag cttcttaact cgaggggaaa catcggtgtc catcctctcg gtgaatcaac    3060
aaatctgtga attgttgttg atttaagaga cgcgttgttt gacatttctc cgtttcgatt    3120
cctctccgtc ccgttcaacc gcattccgcg ttaaacgctt tctgacctat tatgcaatcg    3180
gatgcagact tttgaaagaa cctcttcccc ttttacacg tgtacattgt tcacgatttg      3240
tctatcaatt tgcagatttt tagaatattt tcttatcttg gagaaatatt tacagataaa    3300
gtttgtcatt cgaaatcatt cgatttactt caagatttaa acgtgtgact atattccgcc    3360
tatcaattat attataatcg ttacatcgat tgtgaaatat agatcctcgg aatgtctgct    3420
tgcaaaattc gtcctctcga aatttcgaca atttttaatg ataaatcgat gattatttcg    3480
tttaactcga ttaatgtttc aggccgattt cgacaaagcg tccgtgatgt tttccttcga    3540
caattcccac gtagctatcg gccacgacta cgtgaacgtg agtgatgaca atttttcttt    3600
tctcctctct ctaagaatat ctgataacct ttcctcgact ttttccaggg gtttcgatac    3660
tcgatacacc aaaagtgcac cgtgtacaac attaaatcca ggtgaattat ctacttcttt    3720
tacattacct taccaatatt acgtgtattg ttaaagtctc gctgataaat caaattttc     3780 gaaacagtta ttcgttggca ataacgataa tgttaatgcc ccgatacaca taaataaat     3840 atatatatat acgaatataa taaccgaaaa tataaatgaa aaaaaactcc tatccgaata    3900
ttatggatat agaaaaattg tttatcttct ctttctttct ttctttcccc ttttttttt     3960 ttttttttct tctttcctt tttttcttt tttacatata ccgcagaacg ttcacggata      4020
tcgcgaatgg cgatcgcata ccactgttca aatggtcgcc cacgaggaac gctttgattt    4080
acgttcacaa gaacgatatc tattatcagg tgttcttcga gggtggcagc gacactcgaa    4140
ggataacgaa caccggcgtc ccggacatcg ttttcaacgg gatacccgac tgggtttacg    4200
agggtaaatc gaaagcaacg atggaaaaaa agaaacgaga agagaaaga gggaaacagt      4260 cgaatccgtc cgatcgacga gtaagatcga ttataattaa tcaacgatga tgatttacag    4320
aggaagtgct gggctccccg gtcgcattct ggatctcgcc cgacgacga caccttgctt     4380 tcgccacgtt caacgacacc aacgtccgcg atatcgtgat atctaaatac ggctcccctg    4440
```

-continued

```
gaaactcgag ggatcaatat ccgaacgaga tcaggataaa atatccgaaa gtagatatcc    4500
tcttcgcttt gaacgcgaaa aaacggaagt tggagagatg atcgtaacga aggaattgaa    4560 aaggggatt tttattaact cctcctcctc cagtttcact tttccttcct tagttgtata    4620
catagttgga tccatgtcgc tcaattttcg cgtttcattt ccctttttc gcggagaaga    4680 gaagatacgc gtggaaagag cgggaagatt tttcaattat cttactttct ttctcttttt    4740
ctcctttctc gaattctagg cgggcaccac gaacccattc gtgtccctga gcgtgatcga    4800
cttgcacgat ccctcctcga aattgatcga tcttccgccg cctgtcgatg tcgttggagc    4860
gtgagtatat acacacaaaa gtcacaaaga tctgaattga ctcgttccat tttccctc     4920 gttttatatt ttgtcaaatt tatttgggtt ggcaactaag taattgcgga tttttttta    4980 gaaagtcaaa gacaatttt tcatggaatt aaataagttt attccgcaat gcgttgcccg    5040
ttttgatcaa tgaccttnnn nnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnt ttccattttt caacgaatgc caaaaaactt tttttaccga    5880
ttgacattac tgaattacca actatcgaat aacaaaatgt gttttacatt tggactacgc    5940
cagcaaacct aaagattcaa ctgaagccat ctatgagtga aatccgcaat cacttaattg    6000
ccaacccaat aatttcaata taaactcgat gataaatttc gctagagaaa gttcaacctt    6060
aagatatttc taaaaaaata ttatctctat tcctcttccc agagacaacg ttctttatac    6120
cgcgaactgg aggagggacg gcgagattgt tgcgacgtgg acgaacaggg tgcagaacaa    6180
ggcccaatta gtgctgtacg acactaaggg taacgcgaat aatatttatt acgaggagga    6240
gacggagggt tggcttcgca tccaaccacc cctctatcac gaccgatacg tgatcgttgc    6300
gaagcttcaa gactcgggca cgaaggcggg acggtttctc cacgcgacga ggctcgagta    6360
caggaacggc gccctggtcg acgagacgga tttgacgcct ggaacgtgcg aggttatctc    6420
cctgttgctc gtcgaccacg ccagggccag gctctattac ttgggcaccg agctcggcaa    6480
accatcccac aagaatctct actccgtcca attgagcggc aacgagccgc ccgtttgcct    6540
gtcgtgcgac gtcctcaccc ccgagggtaa gacccatcct tctctccaat tcttctgaat    6600
tctatttaat cacggagggg gaataatttt aaaaacaggg aatcgttgca cctacgccta    6660
cgcctacttc tcgaccaacg gttctcatta cgcgttgtac tgcgccggcc cagaccctgt    6720
cttcatcgcg atagtgaacg cgaatcacag gcagatctcg atttgggagg agaaccgatc    6780
```

-continued

```
ccttaggcgc aagttggccg cccgtacgca gccgattgtc aagaatttca acgtgaacgc   6840
gaacgggtac acgaacaagg ttaagcttta cctgccgccc gacttcgacg agacgaaaaa   6900
gtatcctctg ctgatcaacg tgtgagttgt ttcatcaaat ttgaacggat tatttctcgg   6960
tttatcaatc gagtcgagct gataaacgcc tatttccttc cttcgaagcc aagttttcat   7020
tattgtaaaa acgatcaaga tcttcgagca aatttgaacg aattcaatta atcgagttga   7080
taaataggct tgtttccttc caagattatt cttcttttct ccgcaggtac gcagggccga   7140
acactatcag gattacggag gaggctacgt acgggttcga gtcgtacata gtgacgaaca   7200
ggagcgtaat ttatgggcgc atcgacgggc gtggatcggc gtacaaaggg agcaagatgc   7260
tgttcgagat ctatcgccga ctcggcaccg tggagatcga ggatcagatt attatcacca   7320
ggtggttcat tttgtattcg ccattttatc cttgataagt tagattgtaa cggagttgta   7380
ttgagcagaa cgctgcagga gaagtactcg tggatcgatt cgaacaggac gggcatatgg   7440
ggttggagtt acgcggtttt ctcggccgcc atggtgctgg ccaccgacgc cgagtcggtg   7500
ttcaagtgcg gcatatcagt cgcacccgtc acctcctgga tttattacgg taatttctcg   7560
tacaaaaata cctaaaaaat atcttcttcc tgatattaaa agaatcgaaa tttcttcttt   7620
accgccgtat ggttttctca gattccttgt acacggaacg gttcatgggc ctgccgaccc   7680
cggaggacaa tcagagcggt tacaacgaca cggacgtgag caggagggtg gagggtatgc   7740
gagggaaaaa gtacatgctg atacacggga cagcggacga caacgtgcac taccagcaaa   7800
ccatgatgct gaacaaggct ttggtgaaca gcgacataat gttccagcag cagacgtaca   7860
cggacgaggc gcacgccctc gggaacgtct tcccccatct ctaccacacc atggaccgat   7920
tctgggccaa ttgtctggga tactcccact gattcgttcg gatgaccgat catccgacga   7980
gaaatggtgg atgcgtcccc tttaatcgac catatcccaa ctcgaatcga tcgattcacg   8040
ttcgaatttt cgagaatttt tgagaaaaaa aaaggaaaaa ggatacgttg aatcagaga   8100 ttctcgattc tcgattctgc gttcgacgca gaacgtgtaa gaagttggct tcaaaggga   8160 cggttgaatc gatacttaag aacgcttaag gatgcatttc cgagtgagtg gaaaatggat   8220
cgcggatgga agacgttgta ttttatttt ttcctattta tttcgttctt taatccttac   8280
aatcggctcg ttctatcaaa atttgcgaag agagaggatt tttattacgg atacggtaat   8340 ttttgtcgt ccgccgagat aaatcgttaa taaatccatc ttctttcaag taatttattg   8400
ttacttgttt ttttttaaa tttaaacatt ctttaattgg aaagtaacat ttttgatgat   8460
atttctttga ttttcatttt tcagaaaaga tcgcgtaatt gattagatat ttctcaaagt   8520
ggaattatta attaaaagaa aaattccgag gcacgataaa aaacagagat cacgatcgat   8580
gatactcgtt tttctcttta ctttcaatac gctttttgt tcgatgaacg aatcgaatga   8640
acaagctgaa agtgcattca tctagaattg aaggatttca accggaaatt cgattcatcg   8700
gtgaccattt atttcttttc tgtatccaca gggattacag acatttttt ttttttcct    8760 ctttcaatta tcactcttca cgctcattga aaaccatat tgctcgagat ggaataaaag   8820
agtcgcggaa aaacgttaga aatttgatac gggcaaagta gcatagttat cctatcgaaa   8880 atttaccttaa ccttcaagac tctttctttt tatcctcgta aaaaagaag aatcccttat   8940 ttacttccaa cagactttc ggtataataa tatgacgatt caaaaaaatg tgatcgttga   9000
```

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence; note = synthetic construct

<400> SEQUENCE: 24

```
atggccatct ggtgggaatt atttcgcatt cgattaatgg ttccacgagt gatcgaccag    60
gac                                                                  63
```

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence; note = synthetic construct

<400> SEQUENCE: 25

Met Ala Ile Trp Trp Glu Leu Phe Arg Ile Arg Leu Met Val Pro Arg
1               5                   10                  15

Val Ile Asp Gln Asp
            20

<210> SEQ ID NO 26
<211> LENGTH: 99
<212> TYPE: DNA
<213> ORGANISM: Artificial Sequence
<220> FEATURE:
<223> OTHER INFORMATION: Description of Artificial Sequence; note = synthetic construct

<400> SEQUENCE: 26

```
atggaggtac tggtgcagct ggcgctgctg ctggtggtgc acggatcgct ggtcgtcctc    60
gttgctggaa aatccgttcc acgagtgatc gaccaggac                           99
```

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence; note = synthetic construct

<400> SEQUENCE: 27

Met Glu Val Leu Val Gln Leu Ala Leu Leu Leu Val Val His Gly Ser
1               5                   10                  15

Leu Val Val Leu Val Ala Gly Lys Ser Val Pro Arg Val Ile Asp Gln
            20                  25                  30

Asp

<210> SEQ ID NO 28
<211> LENGTH: 766
<212> TYPE: PRT
<213> ORGANISM: Artificial Sequence
<220> FEATURE:
<223> OTHER INFORMATION: Description of Artificial Sequence; note = synthetic construct

<400> SEQUENCE: 28

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr

```
                 35                  40                  45
Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
                100                 105                 110

Phe Ile Leu Leu Glu Tyr Asn Tyr Val Lys Gln Trp Arg His Ser Tyr
                115                 120                 125

Thr Ala Ser Tyr Asp Ile Tyr Asp Leu Asn Lys Arg Gln Leu Ile Thr
130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
                195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
                275                 280                 285

Ala Pro Ala Ser Met Leu Ile Gly Asp His Tyr Leu Cys Asp Val Thr
                290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
                355                 360                 365

Asn Ser Phe Tyr Lys Ile Ile Ser Asn Glu Glu Gly Tyr Arg His Ile
                370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
                435                 440                 445

Leu Asn Pro Glu Arg Cys Gln Tyr Tyr Ser Val Ser Phe Ser Lys Glu
                450                 455                 460
```

```
Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
            485                 490                 495

Asn Ser Ala Leu Asp Lys Met Leu Gln Asn Val Gln Met Pro Ser Lys
        500                 505                 510

Lys Leu Asp Phe Ile Ile Leu Asn Glu Thr Lys Phe Trp Tyr Gln Met
    515                 520                 525

Ile Leu Pro Pro His Phe Asp Lys Ser Lys Lys Tyr Pro Leu Leu Leu
530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
            565                 570                 575

Ser Phe Asp Gly Arg Gly Ser Gly Tyr Gln Gly Asp Lys Ile Met His
        580                 585                 590

Ala Ile Asn Arg Arg Leu Gly Thr Phe Glu Val Glu Asp Gln Ile Glu
    595                 600                 605

Ala Ala Arg Gln Phe Ser Lys Met Gly Phe Val Asp Asn Lys Arg Ile
610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
            645                 650                 655

Ser Arg Trp Glu Tyr Tyr Asp Ser Val Tyr Thr Glu Arg Tyr Met Gly
        660                 665                 670

Leu Pro Thr Pro Glu Asp Asn Leu Asp His Tyr Arg Asn Ser Thr Val
    675                 680                 685

Met Ser Arg Ala Glu Asn Phe Lys Gln Val Glu Tyr Leu Leu Ile His
690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
            725                 730                 735

Asp Glu Asp His Gly Ile Ala Ser Ser Thr Ala His Gln His Ile Tyr
        740                 745                 750

Thr His Met Ser His Phe Ile Lys Gln Cys Phe Ser Leu Pro
    755                 760                 765

<210> SEQ ID NO 29
<211> LENGTH: 751
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 29

Met Lys Thr Val Val Lys Cys Leu Leu Gly Leu Leu Ala Leu Gly Val
1               5                   10                  15

Ile Ile Thr Ala Ile Val Pro Val Val Leu Leu Thr Arg Asp Asp
            20                  25                  30

Ser Asp Ile Arg Arg Lys Phe Ser Leu Glu Asp Tyr Leu Ser Asp Glu
        35                  40                  45

Phe Gln Tyr Lys Ser Tyr Asn Leu Arg Trp Met Ser Gly His Glu Tyr
```

```
                50                  55                  60
Val Tyr Thr Asn Gln Asn Asn Val Leu Leu Tyr Asn Ile Asp Asp Glu
 65                      70                  75                  80

Arg Glu Ser Ile Val Leu Ser Asn Asp Thr Leu Asp Ser Phe Asn Ser
                     85                  90                  95

Ser Gln Ala Ile Leu Ser Pro Asp Arg Lys Phe Ala Leu Leu Gln Tyr
             100                 105                 110

Ser Tyr Glu Lys Val Trp Arg His Ser Tyr Thr Ala Ser Tyr His Ile
         115                 120                 125

Tyr Asp Leu Asn Asn Arg Thr Lys Ile Thr Glu Asn Pro Leu Pro Thr
130                 135                 140

Asn Ile Gln Tyr Ile Ser Trp Ser Pro Val Gly His Lys Leu Ala Tyr
145                 150                 155                 160

Val Tyr Arg Asn Asn Val Tyr Val Lys Ala Thr Pro Asn Ala Ser Pro
                 165                 170                 175

Val Gln Ile Thr Glu Asn Gly Ala Glu Asn Lys Ile Leu Asn Gly Leu
             180                 185                 190

Ala Asp Trp Val Tyr Glu Glu Met Phe Gly Thr His Ser Ala Leu
         195                 200                 205

Trp Trp Ser Pro Asn Gly Arg Phe Leu Ala Phe Ala Glu Ile Asn Asp
210                 215                 220

Thr Glu Val Pro Val Met Glu Tyr Ser Phe Tyr Ser Glu Asp Thr Leu
225                 230                 235                 240

Gln Tyr Pro Lys Thr Ile Lys Ile Pro Tyr Pro Lys Ala Gly Ala Ile
                 245                 250                 255

Asn Pro Thr Ile Arg Leu Phe Val Leu Asp Ile Ser Leu Ser Pro Lys
             260                 265                 270

Asn Ile Ser Glu Ile Val Ala Pro Ser Ser Ile Ile Ser Gly Asp His
         275                 280                 285

Tyr Leu Ser Ala Val Thr Trp Val Thr Asp Glu Arg Ile Cys Val Gln
290                 295                 300

Trp Leu Arg Arg Ile Gln Asn Phe Ser Val Leu Thr Ile Cys Asp Tyr
305                 310                 315                 320

Ser Gly Ala Trp His Cys Pro Lys Glu Arg Glu His Leu Glu Glu Ser
                 325                 330                 335

Lys Thr Gly Trp Val Gly Arg Phe Gln Pro Ser Glu Pro Tyr Phe Thr
             340                 345                 350

Ser Asp Lys Ile Ser Tyr Tyr Arg Ile Ile Ser Asp Glu Gly Tyr
         355                 360                 365

Lys His Ile His Tyr Thr Asp Ser Ala Gly Lys Val Lys Pro Ile Thr
370                 375                 380

Ser Gly Lys Trp Glu Val Ile Ser Ile Ser Ala Val Thr Asn Asn Ser
385                 390                 395                 400

Leu Tyr Phe Ile Ser Asn Glu Phe Glu Gly Arg Pro Gly Gly Arg His
                 405                 410                 415

Leu Tyr Lys Val Asp Leu Lys Asn Asp Leu Lys Lys Ile Cys Ile Thr
             420                 425                 430

Cys Asn Ser Lys Glu Glu Ala Cys Gln Tyr Phe Ser Val Ser Phe Ser
         435                 440                 445

Thr Asp Ser Arg Tyr Tyr Lys Leu Asn Cys Tyr Gly Pro Asp Leu Pro
450                 455                 460

Tyr Phe Thr Leu Gln Asn Ser Ile Thr Asp Lys Ala Ile Lys Thr Leu
465                 470                 475                 480
```

```
Glu Asp Asn Asn Asn Leu Lys Asn Val Leu Lys Glu Ile Gln Met Pro
                485                 490                 495
Cys Lys Arg Leu Ser Asn Ile Thr Leu His Gly Gln Thr Tyr Trp Tyr
            500                 505                 510
Gln Met Ile Leu Pro Pro Asn Phe Asp Glu Ser Lys Lys Tyr Pro Leu
        515                 520                 525
Leu Ile Asp Val Tyr Ala Gly Pro Cys Ser Gln Lys Ala Asp Ala Ala
    530                 535                 540
Phe Arg Ile Asn Trp Ser Thr Tyr Leu Ala Ser Ser Glu Gly Ile Ile
545                 550                 555                 560
Val Ala Ser Phe Asp Gly Arg Gly Ser Gly Phe Gln Gly Asp Lys Ile
                565                 570                 575
Leu His Ala Ile Tyr Arg Arg Leu Gly Thr Tyr Glu Val Glu Asp Gln
            580                 585                 590
Ile Ser Ala Ala Lys Leu Phe Ser Glu Met Ser Phe Val Asp Lys Asp
        595                 600                 605
Arg Ile Ala Ile Trp Gly Trp Ser Tyr Gly Gly Tyr Val Thr Ser Met
    610                 615                 620
Val Leu Gly Ala Gly Ser Asp Val Phe Lys Cys Gly Ile Ala Val Ala
625                 630                 635                 640
Pro Val Ser Arg Trp Gln Tyr Tyr Asp Ser Ile Tyr Thr Glu Arg Tyr
                645                 650                 655
Met Gly Leu Pro Glu Lys Asn Asp Asn Leu Asn Phe Tyr Glu Asn Ser
            660                 665                 670
Thr Val Met Ala Arg Ala Lys Asn Phe Arg Thr Val Asp Tyr Leu Leu
        675                 680                 685
Ile His Gly Thr Ala Asp Asp Asn Val His Phe Gln Gln Ala Ala Gln
    690                 695                 700
Ile Ser Lys Ala Leu Val Asp Ala Glu Val Asp Phe Gln Ala Met Trp
705                 710                 715                 720
Tyr Thr Asp Lys Asp His Gly Ile Gly Gly His Ala His Ser His Ile
                725                 730                 735
Tyr Gln His Met Ser His Phe Met Lys Gln Cys Phe Lys Leu Pro
            740                 745                 750

<210> SEQ ID NO 30
<211> LENGTH: 156
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 30
aagctttccg ccatggcgaa attcttagtc aacgttgccc ttgtttttat ggtcgtgtac      60
atttcttaca tctatgcggg atccgaccat catcatcatc atcatcatca tcatcattgg     120
ctcgagtcta gaaaatccgt tccacgagtg atcgac                               156

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 31
```

```
tgtctgggat actcccactg ataaccgcgg ttcgaaggta                    40
```

```
<210> SEQ ID NO 32
<211> LENGTH: 48
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 32

Met Ala Lys Phe Leu Val Asn Val Ala Leu Val Phe Met Val Val Tyr
1               5                   10                  15

Ile Ser Tyr Ile Tyr Ala Gly Ser Asp His His His His His His
                20                  25                  30

His His His Trp Leu Glu Ser Arg Lys Ser Val Pro Arg Val Ile Asp
            35                  40                  45
```

CLONING OF HONEY BEE ALLERGEN C

The present application claims priority to European Patent Application No. 06013165.3, filed Jun. 26, 2007, which application is incorporated herein by reference in its entirety.

SUMMARY

The present invention in one aspect relates to a nucleic acid encoding a polypeptide capable of binding to IgE from subjects allergic to venom of an insect from the order *Hymenoptera* having a homology of more than 70% to the amino acid sequence of SEQ ID NO: 2, which is the honey bee allergen C, also referred to as Api m 5 (Ref. 1). The invention further relates to expression vectors, host cells and polypeptides encoded by the nucleic acid, as well as diagnostic and pharmaceutical uses thereof.

BRIEF DESCRIPTION OF THE DRAWINGS

FIG. 1A shows the fractionation of samples by SDS-PAGE and subsequent staining with coomassie blue; Lane 1: bovine serum albumin (BSA); Lane 2: honey bee venom; Lane 3: Enriched Api m 5 fraction; Lane 4: Protein standard (PageRuler™ Protein Standard, Fermentas GmbH). FIG. 1B shows immunoprinting with the samples from (A) and pooled serum from patient allergic to honey bee venom. Detection was performed with anti-IgE alkaline phosphatase conjugate (DPC Alablot system). Lane 1: BSA, negative control; Lane 2: honey bee venom; Lane 3: Enriched Api m 5 fraction; Lane 4: Protein standard (PageRuler™ Prestained Protein Standard, Fermentas GmbH). It can be seen that the sample used for sequencing of Api m 5 (marked by arrow) contains enriched protein that binds to sIgE of honey bee allergic patients).

FIG. 2A shows the GNOMON prediction of Api m 5 N-terminal sequence (SEQ ID NO. 24). Shown is the predicted gene sequence comprising the first exon (base pair 1-39) and part of the adjacent second exon (base pair 40-63). The translated protein sequence (SEQ ID NO. 25) is shown below the nucleic sequence. The predicted signal sequence is marked in italics. Results from SignalP 3.0 server analysis of the predicted N-terminal sequences of Api m 5 revealed the putative signal peptide cleaving site between residues Asp19 and Gln20. The N-terminus of the mature protein is predicted at base pairs 58-60 (Gln). FIG. 2B shows the GeneMark.hmm prediction of Api m 5 N-terminal sequence (SEQ ID NO. 26). Shown is the predicted gene sequence comprising the first exon (base pair 1-6), second exon (base pair 7-75 and part of the adjacent third exon (base pair 76-99). The translated protein sequence is shown below the nucleic sequence (SEQ ID NO. 27). The predicted signal sequence is marked in italics. Sequence analysis delivered a more distinct putative cleavage site between Gly23 and Lys24. The N-terminus of the mature protein is predicted at base pairs 70-73 (Lys) therefore being 8 amino acids longer than the GNOMON prediction extending into exon I. PCR experiments verified the correctness of the GeneMark.hmm prediction.

FIG. 6 shows the nucleic acid sequence of cloned recombinant Api m 5 of 2328 base pair length (SEQ ID NO.1).

FIG. 7 shows the protein sequence of cloned recombinant Api m 5 of 775 amino acid length based on translation of the sequenced nucleic acid sequence (SEQ ID NO. 2).

FIG. 8 shows the isolation of recombinant Api m 5 from transient expression in insect cells. Recombinant Api m 5 from 5 ml supernatant of transfected insect cells was purified by metal-affinity chromatography. The purified protein was submitted to SDS-PAGE and silver stained. Lane 1: PageRuler Protein Standard (Fermentas GmbH, St. Leon-Rot, Germany), Lane 2: Purified recombinant Api m 5. The protein migrates at an apparent molecular weight of approximately 105 kDa with very minor visible contaminants.

FIG. 9 shows the alignment of Api m 5 with other related proteins. Alignment of the sequence with sequences from nucleic acids databases revealed homologies to peptidases from other species. Shown is the alignment of dipeptidylpeptidase IV of the snake *Gloydius blomhoffi brevicaudus* (e.g. Genebank accession AB158224) (SEQ ID NO. 29), human dipeptidylpeptidase IV (e.g. Genenbank accession BC65265) (SEQ ID NO. 28) and honeybee Api m 5. Marked are the residues involved in the conserved active centre of the enzymes.

FIG. 11 shows a comparison of exon structures of the two gene predictions.

DETAILED DESCRIPTION

Figure 1:
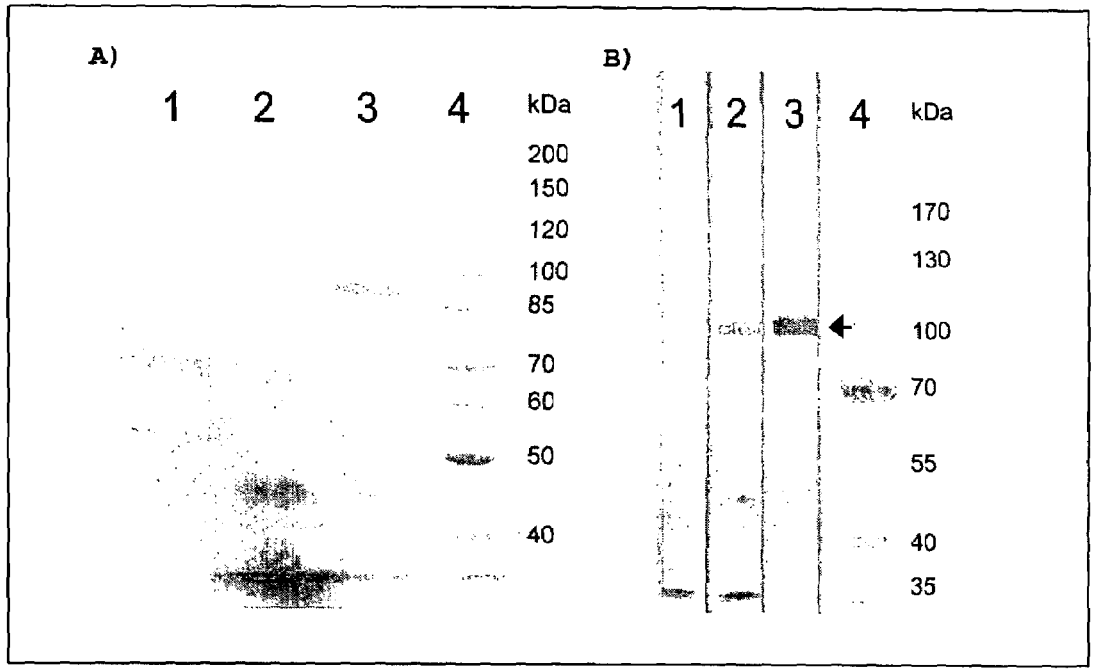
FIG. 1 shows the purification of allergen C (Api m 5) from honey bee venom.

The present invention relates to a nucleic acid encoding a polypeptide capable of binding to IgE from subjects allergic to venom of an insect from the order *Hymenoptera* having a homology of more than 70% to the amino acid sequence of SEQ ID NO: 2, which is the honey bee allergen C, also referred to as Api m 5 (Ref. 1). The invention further relates to expression vectors, host cells and polypeptides encoded by the nucleic acid, as well as diagnostic and pharmaceutical uses thereof.

It has long been recognised that allergies against insect venoms are relatively common. 4-5% of the German population react allergic to insect venoms. In Europe the relevant stinging insects are honey bees (*Apis mellifera*), wasps (*Vespula* spp.), bumble bees (*Bombus* spp.), hornets (*Vespa crabo*), midges, and horse flies (Ref. 2, 3). Bees, bumble bees, wasps, and hornets belong to the order *Hymenoptera*.

These social insects do not normally attack people, but will sting them in self defence if disturbed. Once stung, if the stinger remains in the skin, a honey bee is responsible, while, if no stinger is present, a wasp is likely to be the culprit. The female worker honey bee carries the stinger and dies soon after discharging a sting.

If a bee stings a vertebrate, the stinger will be detached from the insect, but the venom sack will still be attached to the stinger and if not removed, the whole venom volume (up to 50 µl) will be injected into the victim. Wasps can retract the stinger, and only inject about 20 µl venom.

The differences in stinging behaviour are based on natural evolution. Bees collect nectar, whereas wasps and hornets are insect hunters. Therefore, bees need to protect the hive, even against vertebrates like mice or larger animals. The insect dies upon the sting, but will inject the maximum volume of venom, if the stinger is not removed. Wasps and hornets do not have such natural enemies.

Since it is easy to obtain sufficient quantities of material, honey bee venom has been well studied. Honey bee venom contains at least 18 active substances. Melittin, the most prevalent substance, is one of the most potent anti-inflammatory agents known (100 times more potent than hydrocortisone). Adolapin is another strong anti-inflammatory substance, and inhibits cyclooxygenase; it thus has analgesic activity as well. Apamin inhibits complement C3 activity, and blocks calcium-dependent potassium channels, thus enhancing nerve transmission. Other substances, such as compound X, hyaluronidase, phospholipase A2, histamine, and mast cell degranulating protein (MSDP), are involved in the inflammatory response to venom, with the softening of tissue and the facilitation of flow of the other substances. Finally, there are measurable amounts of the neurotransmitters dopamine, norepinephrine and serotonin. The water content varies between 55-70%. The pH range is between 4.5-5.5. A summary of the components of bee venom is given in Table 1 (Ref. 4, 5).

TABLE 1

Listing of bee venom components and composition.

| Component type | Component name | % weight of dry mass |
|---|---|---|
| Proteins | Phospholipase A2 (Api m 1) | 10-12 |
| | Hyaluronidase (Api m 2) | 1-3 |
| | Phosphatase, Glucosidase | 1-2 |
| | Allergen C | <1 |
| Peptides | Melittin (Api m 4) | 50-55 |
| | Secapin, MCD-peptide | 1.5-4 |
| | Tertiapamin, Apamin, Procamin | 2-5 |
| | Other small peptides | 13-15 |
| Biogene amines | Histamine | 0.5-2 |
| | Dopamine | 0.2-1 |
| | Norepinephrine | 0.1-0.5 |
| | Sugars (Glucose, Fructose) | 2 |
| Phospholipids | | 5 |
| Amino acids | | — |
| Volatile substances | Pheromones | 4-8 |
| Minerals | | 3-4 |

The LD50 dose, i.e., the amount of bee venom which causes 50% of the tested individuals to die, is 6 mg venom/kg body weight for mice and rats. This equals 40 stings/kg body weight. For hornets, this factor is around 154-180 stings/kg body weight. Bee venom is 1.7-1.5 more effective than those of hornets (Ref 6, 7).

Honey bees and wasps of the *Hymenoptera* order are by far the most frequent cause of serious allergic reactions. Normally, at least more than 50 stings of a bee per children or 100 per adult are necessary to induce life threatening conditions (see above). In case of allergic persons, one sting can be enough to cause death by adverse immunological reactions.

This type of allergy is mediated by IgE antibodies which react to venom components. The possibility, therefore, exists that desensitisation therapy by repeated and progressively increased doses of bee venom components would be successful. Several polypeptides from bee venom have been cloned and expressed as recombinant molecules (Ref. 8, 9, 10, 11, 12, 13, 14, 15). One component of bee venom, allergen C, also referred to as Api m 5 (Ref. 1), is one of the potent allergic proteins (Ref. 14). In two studies, virtually all tested bee venom allergic sera have been shown to react with allergen C (Ref. 10). One of the tested sera even proved to be monospecific for allergen C (Ref. 14).

As determined by gelelectrophoretic analysis, allergen C has an apparent molecular weight ranging between 102 kDa (Ref. 16) and 105 kDa (Ref. 14). In immunodiffusion, allergen C has been demonstrated to be noncross-reactive with other major bee venom allergens including phospholipase A2 (Api m 1), hyaluronidase (Api m 2), acid phosphatase (Api m 3), and melittin (Api m 4) as well as with other minor components (Ref. 14). The biological function of this protein, however, still remains to be elucidated and until now no sequence information is available. In a recent publication another high molecular weight honeybee venom allergen (apparent molecular weight of 94 kDa) has been proposed to correspond to allergen C (Ref. 17). However, the difference of about 10 kDa does not support this hypothesis. Furthermore, utilizing primers designed on the basis of the N-terminal sequence of this protein (Ref. 17), PCR amplification of honeybee venom gland-derived cDNA did not yield a corresponding product. Therefore, the person skilled in the art is faced with the problem of providing a nucleic acid suitable for recombinant production of allergen C (Api m 5) from the venom of an insect from the order *Hymenoptera*, in particular the honey bee, which can be used for desensitisation therapy as well as in diagnostic tests for the detection of allergy.

This problem is solved by the subject matter of the claims. In particular, the present invention provides a nucleic acid encoding a polypeptide capable of binding to IgE from subjects allergic to venom of an insect from the order *Hymenoptera* wherein the polypeptide has a homology of more than 70% to the amino acid sequence of SEQ ID NO: 2 (note: "SEQ ID NO" relates to code <400> in the attached sequence listing under WIPO standard ST.25).

Preferentially, the degree of homology to the amino acid sequence of SEQ ID NO: 2 is more than 75%, more than 80%, more than 85%, more than 90%, more than 95% or more than 99%. The sequence homology is determined using the clustal computer program available from the European Bioinformatics Institute (EBI). Most preferentially, the polypeptide encoded by the nucleic acid has the amino acid sequence of SEQ ID NO: 2. This polypeptide is designated allergen C (Api m 5). In particular, the nucleic acid comprises or has the nucleotide sequence of SEQ ID NO: 1.

In the context of the present invention, the terms "polypeptide" and "protein" are used interchangeably, without any limitation as to the number of amino acids linked. The polypeptides may also comprise non-naturally occurring amino acids.

Throughout this specification, the polypeptides encoded by the nucleic acid of the invention have to be capable of binding to IgE from subjects allergic to venom of an insect from the order *Hymenoptera*.

Although allergen C (Api m 5) is a very potent allergen, honey bee venom contains only minute amounts of this protein (see Table 1). Therefore, novel procedures for the removal of major venom components such as melittin (50-55% of dry venom mass) had to be developed first to achieve purification of allergen C by SDS-PAGE. However, even from purified allergen C no N-terminal sequence information could be obtained, most likely due to protected N-terminal amino acid residues. After generation of internal allergen C fragments by proteolytic digestion with Lys-C, a few amino acid residues could be identified by subsequent N-terminal sequencing of two peptide fractions isolated by HPLC. One of the amino acid sequences (Pep1, SEQ ID NO: 3), however, turned out to be derived from two peptides, whereas the other (Pep2, SEQ ID NO: 4) contained such a small number of defined amino acid residues that identification of allergen C by database searches, e.g. BLAST was not possible (see also Table 2).

TABLE 2

| Peptide | residues determined by Edman sequencing | | | | | | | | |
|---------|---|---|---|---|---|---|---|---|---|
| Pep1 | A/N | Q | L | P/N | L | Y/N | D | R | D | Q |
| Pep2 | A | X | X | X | N | P | F | V | S | L |

Results of peptide sequencing derived from Lys-C fractionated Api m 5. Two peptides have been isolated by HPLC and submitted to Edman sequencing. Amino acids are given in single-letter code. The amino acids of the first ten positions of the peptides have been determined. X denote positions for which no residues could be determined.

In an alternative approach, the IgE-reactive protein of honeybee venom migrating in SDS-PAGE with an apparent molecular weight of 105 kDa, was digested in-gel with trypsin and the fragments were subjected to sequencing by tandem mass spectrometry (MS-MS sequencing). With the aid of this novel sequencing technology, four peptide sequences (Pep3-6, SEQ ID NO: 5-8) could be identified (see also Table 3).

TABLE 3

| Peptide | residues determined by MS-MS sequencing | | | | | | | | | | | | | | |
|---------|---|---|---|---|---|---|---|---|---|---|---|---|---|---|---|
| Pep3 | V | P | F | N | L | E | E | T | Y | D | Q | S | F | R | — | — |
| Pep4 | E | I | L | Y | S | D | N | Y | V | G | D | I | R | — | — | — |
| Pep5 | N | D | I | Y | Y | Q | V | F | F | E | G | G | S | D | T | R |
| Pep6 | L | G | T | V | E | I | E | D | Q | I | I | I | T | R | — | — |

Results of peptide sequencing derived from in-gel trypsin fractionated Api m 5 and MS-MS sequencing. Amino acids are given in single-letter code. A maximum of 16 amino acids could be determined.

For three of these peptide sequences a BLAST search of the *Apis mellifera* genome yielded perfectly matched hits. Employing the automated gene prediction program GNOMON, the putative gene XP_393818 was predicted to code for the isolated allergen C. A Blast search for short, nearly exact matches, yielded a corresponding result with the fourth peptide sequence. Although under these conditions the search yielded multiple hits, the predicted gene XP_393818 had by far the highest score.

However, utilizing primers designed on the basis of the predicted gene XP_393818, PCR amplification of complete honeybee venom gland-derived cDNA was unexpectedly not successful. Subsequently, since allergen C is a relatively large protein, three sets of primers were used to amplify sections of the protein separately. The 3'-terminal section and the middle section of the predicted nucleotide sequence could be amplified, whereas amplification of the 5'-terminal section was still not successful despite several experimental attempts. The experimental results suggested an erroneous prediction of the 5'-terminus of the allergen C-coding gene. As a result the person skilled in the art is faced with the problem of having no coding sequence available representing the 5'-terminal part of allergen C, and no reliable data from N-terminal Edman sequencing. Therefore, a completely novel identification strategy had to be developed.

Figure 2:
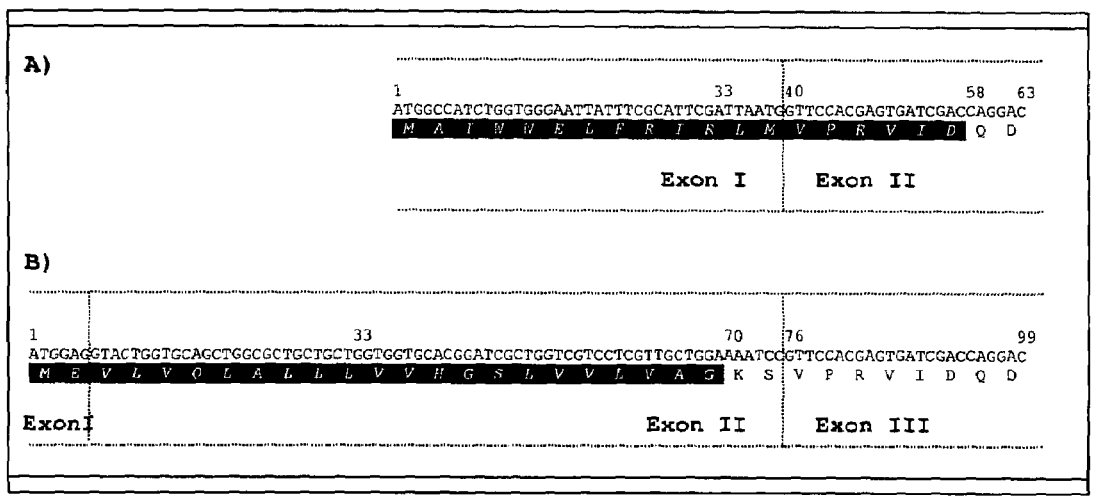
FIG. 2 shows the comparison of predicted N-termini of Api m 5.

Utilizing the novel strategy the four peptide sequences identified by sequencing via tandem mass spectrometry were employed to probe the *Apis mellifera* genome in silico with the TBLASTN protein versus nucleotide search program. Utilizing this program, each of the four sequences yielded a surprisingly perfectly matched single database hit within a single genomic locus (Group 11.11). A segment of the genomic sequence was chosen, having the peptide sequence hits in the middle and stretching 15,000 bp in total length. On the basis of this segment, the eukaryotic gene prediction program GeneMark.hmm unexpectedly predicted a gene with 13 exons coding for a peptidase 775 amino acid residues in length different than that predicted by GNOMON. As assumed, comparison of this predicted gene with predicted gene XP_393818 revealed significant differences in the 5'-terminal segments of both putative genes (see FIGS. 2 and 11).

Figure 4:
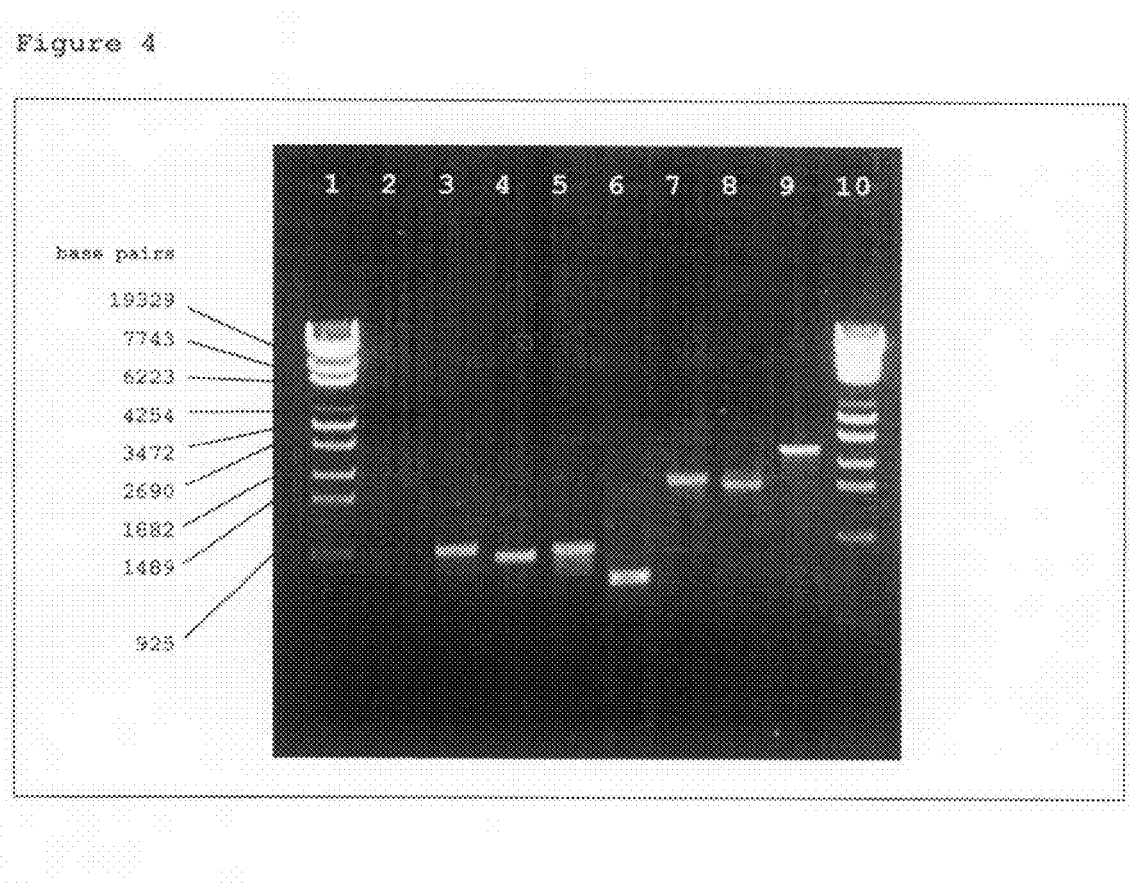
FIG. 4 shows Gel electrophoresis of fragments derived from PCR during cloning of Api m 5 and construction of the insect cell expression vector. Lane 1 shows DNA molecular size standard #16 (Fermentas GmbH, St. Leon-Rot, Germany), Lane 2 shows no bands due to failure of amplification with primer "F1 for GNOMON", Lane 3: amplification of F1 with signal sequence by primers "F1 for GeneMark" and "F1 back". Lane 4: Amplification of fragment F1 without signal sequence by using primer "F1 for pIBXba" Lane 5: Amplification of fragment F2. Lane 6: Amplification of fragment F3. Lane 7: Amplification of hybridised fragment F1-2. Lane 8: Amplification of hybridised fragment F2-3. Lane 9: Amplification of the full length Api m 5 gene without signal sequence from the vector pIB/Api m 5.

Utilizing primer sets designed on the basis of the novel gene predicted by program GeneMark.hmm, PCR amplification of honeybee venom gland-derived cDNA was successful. The set of primers is given in Table 4. Again three sets of primers were used to amplify sections of the protein separately. This strategy proved to be successful and resulted in three DNA fragments of the expected size (see FIG. 4). The identity of the DNA was verified by sequencing. The full length cDNA sequence obtained by ligation of the three cDNA sequences, codes for a protein with a predicted molecular weight of 87.2 kDa. The discrepancy between the deduced molecular weight of allergen C and its apparent molecular weight of 105 kDa, determined by SDS-PAGE analysis, is most likely due to posttranslational modification by glycosylation. The primary sequence of allergen C provides seven potential sites for N-glycosylation.

TABLE 4

Listing of oligonucleotide primers used for amplification of Api m 5 by PCR and sequencing.

| Primer name | Sequence |
|-------------|----------|
| oligodT-20 | 5'-TTT TTT TTT TTT TTT TTT TT (SEQ ID NO: 9) |

TABLE 4-continued

| Listing of oligonucleotide primers used for amplification of Api m 5 by PCR and sequencing. | |
|---|---|
| Primer name | Sequence |
| F3 back | 5'-AAC CGC GGT TAT CAG TGG GAG TAT CCC AGA CA (SEQ ID NO: 10) |
| F3 for hyb | 5'-GAA AAA GTA TCC TCTGCT GAT CAA CGT GTA CGC AGG GCC GAA CAC TAT CAG GAT TAC (SEQ ID NO: 11) |
| F2 back | 5'-GCC TCC TCC GTA ATC CTG ATA GTG TTC GGC CC (SEQ ID NO: 12) |
| F2 for | 5'-CGG GCA CCA CGA ACC CAT TCG TGT CCC TGA GCG (SEQ ID NO: 13) |
| F1 back | 5'-AGA ACG TTG TCT GCT CCA ACG (SEQ ID NO: 14) |
| F1 for GNOMON | 5'-ATG GCC ATC TGG TGG GAA TTA TTT CGC ATT CGA (SEQ ID NO: 15) |
| F1 for GeneMark | 5'-ATG GAG GTA CTG GTG CAG CTG GCG CTG CTG CTG (SEQ ID NO: 16) |
| F1 for pIBXba | 5'-GAT CTC TAG AAA ATC CGT TCC ACG AGT GAT CG (SEQ ID NO: 17) |
| F2 back pIBNot | 5'-GAT CGC GGC CGC GCC TCC TCC GTA ATC CTG ATA GTG TTC GGC CC (SEQ ID NO: 18) |
| M13/Uni for | 5'-GTA AAA CGA CGG CCA GTG CCA A (SEQ ID NO: 19) |
| M13/Uni back | 5'-CAG GAA ACA GCT ATG ACC ATG A (SEQ ID NO: 20) |
| OpIE2 for | 5'-CGC AAC GAT CTG GTA AAC AC (SEQ ID NO: 21) |
| OpIE2 back | 5'-GAC AAT ACA AAC TAA GAT TTA GTC AG (SEQ ID NO: 22) |

The social insects from the order *Hymenoptera* that commonly interact with man are members of the superfamilies *Apoidea* and *Vespoidea*, bees and wasps (Ref. 18). The Vespoidea include the social wasps and hornets, *Vespidae*, as well as ants, *Formicidae*. Important wasps comprise yellowjackets of the genus *Vespula*, bold-faced hornets of the genus *Dolichovespula*, hornets of the genus *Vespa* and paper wasps of the genus *Polistes*. Bees comprise, e.g., honey bees, *Apis mellifera*, and bumble bees of the species *Bombus terrestris*. In the context of the present invention, an insect from the order *Hymenoptera* can be from any of these species, but according to a particular embodiment, the insect is a bee from the genus *Apis*. Most preferably, the bee is the honeybee, *Apis mellifera*.

Other species from the order *Hymenoptera* produce similar allergens with antigenic cross reactivity and a high degree of amino acid homology (Ref. 19, 20, 21). Thus the present invention not only extends to allergen C (Api m 5) from *Apis mellifera* but also to homologous *Hymenoptera* allergens.

In particular, the polypeptides encoded by the nucleic acids of the invention have to be capable of binding to IgE from subjects allergic to venom of *Apis mellifera*. The subjects are commonly reactive to antigen C from bee venom. For the purpose of testing, serum or purified IgE from such allergic subjects are contacted with the polypeptide, and specific binding of the polypeptide to the antibodies is detected. Such a test can, e.g., be an ELISA or an immunoprinting experiment. For verifying the reactivity of the polypeptides with IgE antibodies, serum or IgE from several subjects are pooled, preferentially, from 5 to 20 subjects.

The nucleic acids of the invention can be either DNA or RNA. In one embodiment, the invention also provides a nucleic acid, which is a fragment having a length of more than 528 nucleotides of a nucleic acid encoding a polypeptide having a homology of more than 70% to the amino acid sequence of SEQ ID NO: 2, wherein the fragment encodes a polypeptide capable of binding to IgE from subjects allergic to venom of an insect from the order *Hymenoptera*. Preferably, the nucleic acid is a fragment having a length of more than 582 (25%), more preferably of more than 1164 (50%), more than 1629 (70%) or more than 1863 (80%) nucleotides of a nucleic acid encoding a polypeptide having the amino acid sequence of SEQ ID NO: 2.

In another embodiment, a nucleic acid fragment (polynucleotide) is provided that comprises at least 15 contiguous nucleotides of the nucleic acid encoding a polypeptide having the amino acid sequence of SEQ ID NO: 2. Alternatively, the nucleic acids encode polypeptides that are capable of binding to IgE from subjects allergic to venom of an insect from the order *Hymenoptera*, and comprise at least 15, preferably at least 18, 21, 24, 27, 30, 45, 60 or more nucleotides of a nucleic acid more than 70%, more than 80% or more than 90% homologous or identical to the nucleic acid shown in SEQ ID NO: 1.

Alternatively, a nucleic acid is provided which encodes a polypeptide having more than 70% homology to the polypeptide encoded by said at least 15 contiguous nucleotides, wherein the polypeptide is capable of binding to IgE from subjects allergic to venom of an insect from the order *Hymenoptera*. Alternatively, the polypeptides encoded by the nucleic acids are capable of binding to IgE from subjects allergic to venom of an insect from the order *Hymenoptera*, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2.

In one embodiment, the invention also provides a polypeptide encoded by a nucleic acid of the invention. Preferentially, the polypeptide is full length allergen C from the venom of an insect from the order *Hymenoptera*. In particular, the polypeptide has an homology of more than 70%, more than 75%, more than 80%, more than 85%, more than 90%, more than 95% or more than 99% to the amino acid sequence of SEQ ID NO: 2. Most preferred is a polypeptide having the amino acid sequence of SEQ ID NO: 2.

Although not essential, it is preferred that the polypeptide has peptidase activity, in particular dipeptidyl peptidase activity. This activity can be tested, e.g., according to the method described in (Ref. 22, 23). The purified recombinant Api m 5 showed a dipeptidyl peptidase activity as suggested by alignment of the sequence.

Alternatively, the polypeptide is a fragment of the full length protein capable of binding to IgE from subjects allergic to venom of an insect from the order *Hymenoptera* having a length of more than 194 (25%), more than 388 (50%) or more than 543 (79%) amino acids. Alternatively, the polypeptides are capable of binding to IgE from subjects allergic to venom of an insect from the order *Hymenoptera*, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2.

Preferably, the polypeptide of the invention is recombinantly expressed. This has the advantage, e.g., that the polypeptide can be expressed as a fusion protein linked to an additional polypeptide. For example, the polypeptide or fusion protein is attached to a signal sequence ensuring its secretion into the extracellular space or supernatant of the cultured cells, where appropriate. Due to novel techniques in molecular biology, the use of recombinant proteins in therapy and diagnostics is expected to increase the efficiency and diagnostic value in these medical applications (Ref. 24, 25, 26).

Depending on the host cell producing the recombinant protein, the protein is glycosylated (after expression in mammalian or yeast cells) or non-glycosylated (after expression in bacterial cells). The glycosylation pattern can vary depending on the host cell used, and can thus differ from the glycosylation pattern of natural antigen C isolated from bee venom. In one alternative, the glycosylation pattern is identical to the glycosylation pattern of antigen C isolated from bee venom. Glycosylation can have profound effects on the binding of specific antibodies.

When expressed in bacterial cells, the polypeptide of the invention lacks glycosylation. The protein thus differs from the native protein in respect to epitope presentation, and potentiality for folding and functionality. It was shown that carbohydrates can represent IgE epitopes and contribute to observed non-specific cross-reactivity of allergens, e.g., between bee and wasp proteins, due to similar features of the carbohydrate chains (Ref. 27, 28, 29). The cross-reactivity is one reason for false positive results in in vitro immunological tests (Ref. 30). Expression of the non-glycosylated polypeptide eliminates these false positives, and can therefore be used to advantage in diagnostic and therapeutic applications.

The glycosylation pattern in eukaryotic cells other than insect cells, e.g., in mammalian cells, also varies from the glycosylation pattern of the native protein (Ref. 31). Even in insect cells, the glycosylation pattern is likely to be different due to overexpression of the protein.

Sequence analysis of antigen C (Api m 5) shows that the protein comprises seven putative glycosylation sites of the sequence Asn-Xaa-Ser/Thr. In one embodiment, the polypeptides of the invention comprise mutated glycosylation sites instead of glycosylation sites. In particular, in a mutated glycosylation site, the asparagine (Asn) in the glycosylation site(s) can be exchanged against any other amino acid, preferably against glutamine (Gln) (Ref. 32). Alternatively, in a mutated glycosylation site, the serine (Ser) can be exchanged against another amino acid or deleted. Accordingly, the invention also provides a nucleic acid encoding a polypeptide of the invention comprising at least one, preferably 2, or more mutated glycosylation sites instead of glycosylation sites. Most preferably, all glycosylation sites are mutated.

The present invention also relates to an expression vector comprising a nucleic acid of the invention operationally linked to an expression control sequence. In one alternative, the nucleic acid is linked in frame to a nucleic acid encoding an additional polypeptide, so the expression vector can be used for expression of a fusion protein. The additional polypeptide can be selected from the group comprising a poly-histidine tag (His-tag), glutathione-S-transferase, β-galactosidase, a cytokine, and an IgG-Fc. In particular, tags that simplify purification of the recombinant protein, e.g., a His tag, are employed. Such a tag may be cleaved off after purification of the protein.

Alternatively, it can be beneficial for therapeutic applications to express the polypeptide of the invention linked to a therapeutic polypeptide, e.g. a cytokine. For example, a fusion protein with a cytokine enhancing $T_H1$ and down-regulating $T_H2$ responses or inducing class switch to IgG, such as IFN-□, IL-10, IL-12 or TGF-□, can improve efficiency of desensitisation. If the expression vector is used for gene therapy, it is envisaged to use sequences rich in CpG (unmethylated cytosine guanidine dinucleotides), which promote $T_H1$ responses. Additionally or alternatively, the polypeptide of the invention can be linked to another polypeptide or protein, such as in the form of a fusion protein or as separate proteins expressed by the same vector. Preferably, the further polypeptides or proteins are other *Hymenoptera* venom proteins or antigenic fragments thereof.

The expression vector can be suitable for expression in different cell types, such as bacterial, yeast or mammalian cells. Preferentially, the vector is suitable for expression in insect cells, e.g., HighFive insect cells (Invitrogen GmbH, Karlsruhe, Germany). Alternatively, especially for gene therapy applications, the vector is suitable for expression in human cells. In this context, the expression of the encoded polypeptide can be directed by the choice of a suitable expression control sequence, e.g., an expression control sequence mainly or specifically operational in different cell types, such as lymphoid cells, for example dendritic cells, B cells or macrophages.

In one embodiment of the invention, the expression vector is pIB/V5-His (Invitrogen GmbH, Karlsruhe, Germany, Invitrogen Manual: InsectSelect BSD System with pIB/V5-His, Version G, 30 May 2003).

Figure 3:
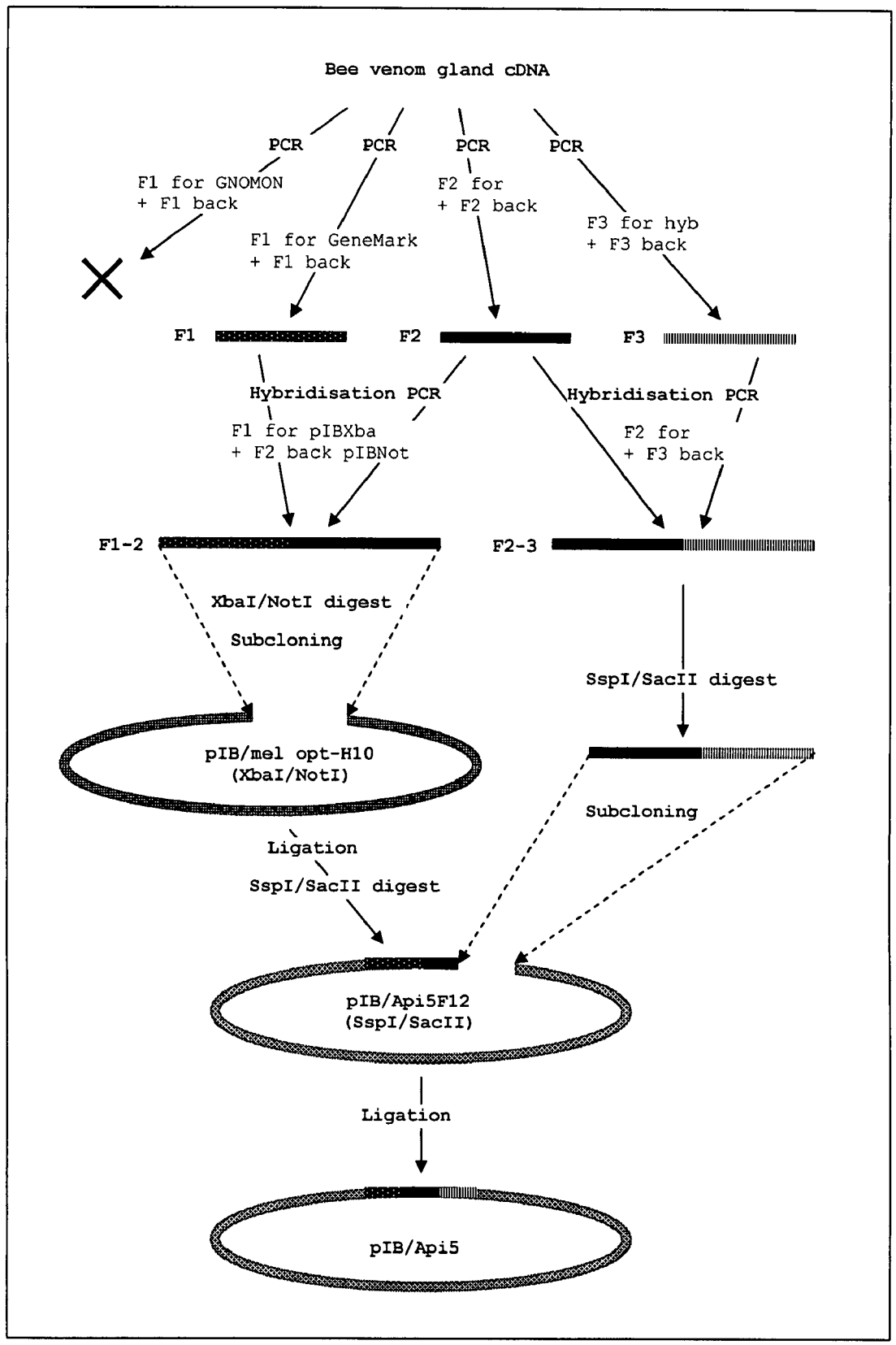
FIG. 3 shows the Schematic overview of the cloning of Api m 5 and construction of the insect cell expression vector pIB/Api5.
Figure 5:
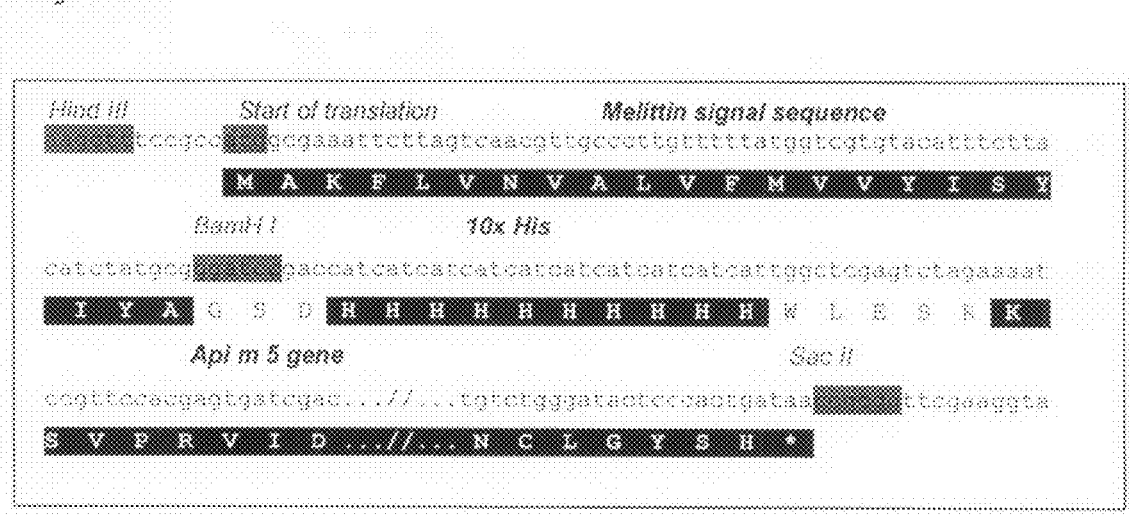
FIG. 5 shows the schematic representation of the nucleic acid sequence (SEQ ID NO. 30 and 31) of the multiple cloning site of pIB/Api5 for expression of recombinant Api m 5 with His-tag for a simplified purification strategy. The translated protein sequence is shown below the nucleic sequence (SEQ ID NO. 32)

In particular, the vector can be pIB/Api m 5 comprising the Api m 5 cDNA sequence (Seq ID NO: 1), which was modified to facilitate isolation and purification. The vector construct pIB/Api m 5 is based on the insect cell expression vector pIB/Mel opt-H10 described in Grunwald et al 2006 (Ref 42). Detailed information of the construction of the pIB/Api m 5 expression vector is given in Example 5.5. A melittin signal sequence for secretion of the recombinant protein was added and the Kozak sequence was optimised for higher expression rates in insect cells. Alternatively, other signal sequences can be used for secretion of the protein. The expression vector can also be a different plasmid or a viral, e.g., baculoviral or adenoviral, vector. The expression vector further comprises a stop codon and a polyadenylation signal (see also FIGS. 3 and 5).

The present invention further relates to a host cell comprising said expression vector. This host cell can be a bacterial, yeast or mammalian cell, in particular an insect cell.

A method of producing a polypeptide encoded by a nucleic acid of the invention is provided, wherein the host cell is cultured under appropriate conditions for expression of said polypeptide and said polypeptide is purified. If the polypeptide is a fusion protein with a fusion partner facilitating purification, e.g., a His Tag or a GST-tag, a corresponding affinity column can be used for purification, e.g., a $Ni^{2+}$ or glutathione affinity column. For purification of an IgG fusion protein, a protein A or protein G column is suitable.

The expression vector of the invention can be used for the preparation of a pharmaceutical composition for treating subjects allergic to the venom of an insect from the order

*Hymenoptera*. Treatment regimens using gene therapy approaches to desensitisation are known in the state of the art (e.g., Ref. 33).

The invention thus also provides a method of treating subjects allergic to the venom of an insect from the order *Hymenoptera* comprising administering to a subject with such an allergy an expression vector of the invention. The expression vector can be administered directly, e.g., by intravenous, intramuscular or subcutaneous injection, gene gun or together with cells taken from the subject which were transfected ex vivo.

As used herein, "subject" encompasses human subjects (patients), grown-ups as well as children, and animals.

A pharmaceutical composition comprising an expression vector of the invention, and, optionally, comprising a suitable adjuvant or expedient, can be employed for this purpose. In particular, this expression vector is rich in CpG sequences and/or encodes a cytokine which shifts the balance between $T_H1$ and $T_H2$ immune responses.

Alternatively, the polypeptide of the invention is used for the preparation of a pharmaceutical composition for treating subjects allergic to the venom of an insect from the order *Hymenoptera*. The invention thus provides a method of treating subjects allergic to the venom of an insect from the order *Hymenoptera*, comprising administering a polypeptide of the invention to a subject having such an allergy.

Desensitisation approaches are well known in the state of the art. In principle, repeated treatments of allergic individuals with suitable, normally progressively increased doses of allergen diverts the immune response to one dominated by T cells that favour the production of IgG and IgA antibodies over production of IgE antibodies. The IgG and IgA antibodies are thought to desensitise the subject by binding to the small amounts of allergen normally encountered, and preventing the allergen from binding to IgE. Desensitisation to insect or bee venom is almost universally successful (Ref. 34). Different protocols and time schedules can be used, from traditional protocols, rush protocols to ultrarush protocols (e.g., Ref. 35), all of which are incorporated herein by reference. The efficacy of such protocols can be evaluated by testing the adjustment of IgE and IgG (different isotypes) and/or IgA levels in the subject's blood or by challenging the subject in a controlled manner and determining the allergic response.

The polypeptide of the invention can be administered alone or combination with other allergens, e.g. other *Hymenoptera* venom proteins or fragments thereof. In particular, combinations with bee or *Hymenoptera* venom phospholipase A2, hyaluronidase, acid phosphatase, glucosidase and/or mellitin are suitable, as this therapy induces generation of IgG/IgA antibodies to several venom allergens and can thus lead to full protection. The identified bee allergens are shown in Table 5.

TABLE 5

Listing of identified bee allergens.

| Allergen | Common name | Size (processed) | Weight | Swiss Prot | Reference |
|---|---|---|---|---|---|
| Api m 1 | Phospholipase A2 | 134 aa | 15.2 kDa | P00630 | Kuchler et al 1989 |
| Api m 2 | Hyaluronidase | 349 aa | 40.7 kDa | Q08169 | Gmachl and Kreil 1993 |
| Api m 3 | Acid Phosphatase | 373 aa | 45 kDa | Q4TUB9 | Grunwald et al 2006 |
| Api m 4 | Melittin | 26 aa | 2.8 kDa | P01501 | Vlasak et al 1983 |
| Api m 5 | Allergen C | nd aa | 105 kDa | — | Hoffman et al 1977 |
| Api m 6 | — | 71 aa | 7.5 kDa | P83563 | Kettner et al 2001 |

The polypeptide of the invention can also be used for the preparation of a diagnostical composition for diagnosing or identifying subjects allergic to the venom of an insect from the order *Hymenoptera*. A method of diagnosing an allergy to venom of an insect from the order *Hymenoptera* is thus provided, comprising the steps of a) contacting a subject with a polypeptide of the invention and b) detecting an allergic reaction, wherein detecting an allergic reaction indicates said allergy.

In vivo tests for diagnosis of an allergy can easily be adapted to the polypeptide of the invention. Typically, a suitable amount of allergen is injected subcutaneously into a subject's limb, and, after a certain amount of time, the degree of localised inflammation in comparison to controls is determined (skin prick test). Such tests are well known in the art (Ref. 36, 37, 38, 39, 40).

An allergy to the venom of an insect from the order *Hymenoptera* can also be diagnosed by an in vitro method comprising the steps of a) in vitro contacting a blood sample from a subject with a polypeptide of the invention and b) detecting binding of IgE antibodies to the polypeptide, wherein detecting IgE antibodies binding to the polypeptide indicates said allergy.

Binding of IgE antibodies to the polypeptide can, e.g., be detected in an ELISA or by an in vitro release assay employing stripped mast cells and measuring the amount of released mediator, e.g., histamine. To determine specific binding, the results are compared with a specificity control, e.g., with an unrelated antibody. The diagnostic tests can in parallel be carried out to determine the levels of specific IgG (in particular IgG1 and/or IgG4) and/or IgA. For this, an ELISA with specific secondary antibodies recognising the different isotypes can be employed. Parallel testing is particularly useful for following and evaluating a course of specific immunotherapy.

For the therapeutic and diagnostic uses and methods, it is preferred to employ the fusion polypeptides of the invention, non-glycosylated proteins or polypeptides that are capable of binding to IgE from subjects allergic to venom of an insect from the order *Hymenoptera* and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2.

The invention thus also provides a pharmaceutical or diagnostical composition comprising the polypeptide of the invention. Preferentially, the composition further comprises a suitable adjuvant and/or expedient. Optionally, the composition additionally comprises other bee or *Hymenoptera* venom polypeptides, such as phospholipase A2, hyaluronidase, acid phosphatase, glucosidase and/or mellitin.

The present invention also relates to a method of diagnosing an allergy to venom of an insect from the order *Hymenoptera*, comprising the steps of a) performing the method of producing a polypeptide encoded by the nucleic acid of the invention, wherein the host cell comprising the expression vector of the invention is cultured under appropriate conditions for expression of said polypeptide, and wherein said polypeptide is purified, b) contacting the polypeptide obtained by the method of step a) in vitro with a blood sample, c) and detecting binding of IgE antibodies to the polypeptide, wherein detecting IgE antibodies binding to the polypeptide indicates said allergy.

Furthermore, a method of diagnosing an allergy to venom of an insect from the order *Hymenoptera* is provided, comprising the steps of a) performing the method of producing a polypeptide encoded by the nucleic acid of the invention, wherein the host cell comprising the expression vector of the invention is cultured under appropriate conditions for expression of said polypeptide, and wherein said polypeptide is purified, b) contacting a subject with the polypeptide obtained by the method of step a) and detecting an allergic reaction, and c) detecting an allergic reaction, which is indicative of the allergy.

The invention also provides a method of preparing a composition for diagnosing an allergy to venom of an insect from the order *Hymenoptera* comprising the step of producing a polypeptide encoded by the nucleic acid of the invention, wherein the host cell comprising the expression vector of the invention is cultured under appropriate conditions for expression of said polypeptide and said polypeptide is purified and can be used as such for diagnosis. Optionally, the polypeptide is further formulated with stabilizers, such as a neutral protein (e.g., BSA) or detergents to give said composition.

In another embodiment, the invention teaches a method of preparing a composition for treating subjects allergic to the venom of an insect from the order *Hymenoptera*, comprising the step of performing the method of producing a polypeptide encoded by the nucleic acid of the invention, wherein the host cell comprising the expression vector of the invention is cultured under appropriate conditions for expression of said polypeptide and said polypeptide is purified and can be used as such for therapy. Optionally, the polypeptide is further formulated with appropriate excipient and/or carriers in order to provide said composition. Correspondingly, a method of treating subjects allergic to the venom of an insect from the order *Hymenoptera* is disclosed, comprising the steps of a) performing the method of producing a polypeptide encoded by the nucleic acid of the invention, wherein the host cell comprising the expression vector of the invention is cultured under appropriate conditions for expression of said polypeptide and said polypeptide is purified, and b) administering the polypeptide obtained by the method of step a) to a subject having such an allergy.

The present invention thus for the first time satisfies the need for a recombinantly produced *Hymenoptera* venom allergen C or the cDNA encoding this polypeptide, which can be used for diagnostic and therapeutic applications.

EXAMPLES

Example 1

Enrichment of Api m 5

1.1 Enrichment of Api m 5

200 mg of lyophilized honey bee venom (Latoxan, Valence, France) were dissolved in 10 ml of 30 mM sodium citrate buffer (pH 4.5). Following removal of insoluble components by centrifugation at 4000×g for 30 minutes the supernatant was incubated overnight with 5 ml of Sephadex C-25 ion exchange resin (GE Healthcare, Chalfont St. Giles, UK) pre-swollen in the same buffer. After settling of the resin by centrifugation, the supernatant was recovered and reduced to 800 µl by lyophilization, dialyzed against 3 mM Tris-HCl buffer (pH 7.0) and further reduced to 300 µl. This step enriches the approx. 100 kDa Api m 5 in relation to the abundant lower molecular weight protein fraction containing melittin and phospholipase A2.

1.2 Isolation of Api m 5

The enriched protein sample was subjected to fractionation by sodium dodecyl sulfate polyacrylamide gel electrophoresis (SDS-PAGE). After addition of 100 µl of 4× reducing PAGE sample buffer the sample was denatured by heating to 95° C. for 5 minutes and then separated on a 10% PAGE mini-gel slab (8×10 cm) poured with 10-sample-well comb. Under these conditions the 100 kDa protein band could be clearly separated from other components in the bee venom. The visualization of protein bands was achieved by submerging the gel for 30 minutes in coomassie staining solution (0.1% coomassie brilliant blue G-250, Merck KGaA, Darmstadt, Germany; 10% acetic acid; 45% methanol), followed by incubation for 2 h in destaining solution (20% acetic acid). To estimate the apparent molecular weight a protein standard (PageRuler™ Protein Ladder, Fermentas GmbH, St. Leon-Rot, Germany) was separated in parallel on the SDS-PAGE gel. The staining with coomassie was omitted if the gel was subsequently used for Western blotting (see FIG. 1).

1.3 Verification of Allergic Potential

Immunoprinting was performed to verify the allergic potential of enriched Api m 5. Two SDS-PAGE gel slabs with each containing samples of bovine serum albumin, honey bee venom and bee venom enriched in Api m 5, were run and eletroblotted onto a nitrocellulose membranes (Protran™, Whatman GmbH, Dassel, Germany). The nitrocellulose membranes were pre-equilibrated in transfer buffer (20 mm CAPS, pH 11, 10% (v/v) methanol). Transfer was done at 50V for 3 hours submersed in blotting buffer in a blotting chamber (model TE22, Amersham Pharmacia, Freiburg, Germany) according to the instructions of the manufacturer. One membrane was subsequently stained with coomassie brilliant blue G250 according to the instructions of the manufacturer. The other membrane was blocked in phosphate buffered saline (20 mM sodium phosphate, 150 mM NaCl, pH 7.5) with 1% (w/v) polyvinyl alcohol 30.000-70.000 (PVA, Sigma-Aldrich Chemie GmbH, Munich, Germany) and 1% (w/v) polyvinyl alcohol 145.000 (Merck Schuchardt OHG, Hohenbrunn, Germany) for 1 hour. The membrane was cut into strips each containing one sample. Using the AlaBLOT system kit (DPC Biermann GmbH, Bad Nauheim, Germany) blocked sample strips were incubated with pooled serum from honey bee allergic patients diluted 1:10, washed and analyzed for binding of anti-IgE antibodies. The result showed that the enriched 100 kDa band (Api m 5), designated for sequencing, exhibited the allergic potential as seen in whole bee venom (see FIG. 1).

Example 2

N-terminal Sequencing of Blotted Sample 2.1 Western Blotting

A SDS-PAGE gel slab with fractionated bee venom enriched in Api m 5 was obtained as described in Example 1.2 and electroblotted onto a PVDF membrane (ProBlott™, Applied Biosystems, Foster City, Calif., USA). The PVDF membrane was pre-wetted in methanol and pre-equilibrated in transfer buffer (20 mm CAPS, pH 11, 10% (v/v) methanol). Transfer was done at 50V for 3 hours submersed in blotting buffer in a blotting chamber (model TE22, Amersham Pharmacia, Freiburg, Germany) according to the instructions of the manufacturer. The membrane was subsequently stained with coomassie brilliant blue G250 according to the instructions of the manufacturer. The area on the membrane containing the band of interest (apparent molecular size of approximately 100 kDa) was excised using a sterile scalpel.

2.2 N-terminal Sequencing

The excised membrane with immobilized protein was used as sample for N-terminal sequencing by Edman degradation on a Protein Sequencer 476 (Applied Biosystems, Foster City, Calif., USA) according to the instructions of the manufacturer. No sequence data was obtained, suggesting a naturally occurring N-terminal modification of the target protein.

Example 3

Peptide Sequencing

N-terminal blocking of the target protein required fragmentation of the protein prior to sequencing of internal peptides.

3.1 Preparation of Sample

The bands in the gel slab obtained as described in 1.2 were visualized by coomassie staining. After staining, the band of apparent 100 kDa molecular size was excised. The excised gel piece was cut into smaller pieces, washed 4× with 500 µl 50% acetonitrile for 20 minutes and subsequently freeze dried.

3.2 Enzymatic Fragmentation

Lyophilized gel pieces were rehydrated with digestion buffer (25 mM Tris-HCl, pH 8, 1 mM EDTA) and subsequently just barely covered with buffer containing 25 µg/ml Lys-C protease (Roche Diagnostics GmbH, Penzberg, Germany) and then incubated at 37° C. for 18 hours. The supernatant was removed and the gel pieces washed 3× with 500 µl 50% acetonitrile for 20 minutes. Supernatant and washes were pooled, reduced to 200 µl in a vacuum centrifuge (SpeedVac™ concentrator, Savant) extracted twice with 200 µl 3-methylbutanol and further reduced to 20 µl in a vacuum centrifuge.

3.3 Peptide Separation

The sample was separated by HPLC on a Vydac C4 column (250×2.1 mm) using a 0-70% gradient of acetonitrile in water with a flow rate of 200 µl/min and peaks fractionated according to absorbance at 280 nm.

3.4 N-terminal Sequencing 2 fractions obtained by HPLC were sequenced by Edman degradation on a Protein Sequencer 476 (Applied Biosystems, Foster City, Calif., USA) according to the manufacturers instructions. The obtained partial sequences of peptides Pep1 (SEQ ID NO:3) and Pep2 (SEQ ID NO:4) are given in Table 2. The sequence information was not sufficient to identify the protein.

Example 4

Tandem-MS Sequencing 4.1 Preparation of Sample

The bands in the gel slab obtained as described in 1.2 were visualized by coomassie staining (see Example 3.1) and the band of apparent 100 kDa size was excised.

4.2 MS-MS Sequencing

The sample was digested in-gel by sequencing grade trypsin (Roche Diagnostics GmbH, Penzberg, Germany) and resulting peptide fragments were sequenced on a Waters Micromass QToF2 mass spectrometer (Waters, Milford, Mass., USA) by tandem mass spectrometry, both steps according to the manufacturers instructions. The obtained sequences of 4 peptides are given in Table 3.

4.3 Database Search

A BLAST search of an annotated *Apis mellifera* genome assembly available from NCBI (Ref. 41) yielded a single, perfectly matched hit for Pep3 (SEQ ID NO:5), Pep4 (SEQ ID NO:6) and Pep5 (SEQ ID NO:7): XP_393818. No BLAST hits were found for Pep6 (SEQ ID NO:8), however, a BLAST search for short, nearly exact matches yielded multiple hits, XP_393818 having the highest score by a large margin. XP_393818 is a predicted gene derived from automated gene prediction using the GNOMON tool.

After a PCR amplification using the gene information derived from the XP_393818 failed, the peptide sequences were used to probe the *Apis mellifera* genome using a TBLASTN protein vs. nucleotide search (Human Genome Sequencing Center, Baylor College of Medicine, available at http://www.hgsc.bcm.tmc.edu; default settings). Sequences Pep3, Pep4 Pep5 and Pep6 each yielded a single perfectly matched database hit, gnl|Amel_2.0|Group 11.11 (corresponding to NCBI Genebank accession No. NW_622532 (GI:66520095)), suggesting this is the locus of the gene encoding the sequenced protein. A segment of gnl|Amel_2.0|Group 11.11 15000 bp in length (a 9000 bp (bp 322000-331000) segment of this sequence comprising the center portion of the matching sequences is shown as SEQ ID NO: 23) centered on the hit for Pep3-6 was used for eukaryotic gene prediction using GeneMark.hmm (Georgia Institute of Technology, Atlanta, Ga.; available online at http://exon.gatech.edu/GeneMark/). Prediction yielded only one gene of the expected size. The predicted gene contains 13 exons coding for a protein 775 amino acids in length. The PCR based on the revised prediction yielded the expected fragments of Api m 5 (see Example 5.3).

The amino acid sequence was submitted to a SignalP-server (Center for Biological Sequence Analysis, Technical University of Denmark, Lyngby, Denmark, available at http://www.cbs.dtu.dk/services/SignalP/; default settings) to check for the presence of a potential signal peptide. Results strongly suggest the presence of a signal peptide with a cleavage site located between positions 23 and 24 (see FIG. 2).

Example 5

Cloning of cDNA 5.1 Total RNA Isolation

Total RNA was isolated from the separated stingers of 2 honey bees with attached venom sack and additional glands. The isolation of total RNA was performed using a kit according to the manual (peqGold TriFast™, peqlab Biotechnologie GmbH, Erlangen, Germany). The organs were weighed and homogenised in a solution containing guanidinium isothiocyanate and phenol. Phase separation was induced by addition of chloroform. The aqueous phase was separated after centrifugation, and the containing RNA was precipitated with isopropyl alcohol. After washing with diluted ethanol the RNA was dissolved in RNase-free sterile water and used directly in RT-PCR experiments. To prepare RNase-free sterile water cell-culture suitable water was treated with 0.1% (v/v) diethylpyrocarbonate (DEPC) overnight, and then autoclaved for 20 minutes to destroy DEPC by causing hydrolysis of DEPC.

5.2 cDNA First Strand Synthesis

Superscript III™ reverse transcriptase kit (Invitrogen GmbH, Karlsruhe, Germany) was used to synthesise first strand cDNA from the isolated RNA according to the instructions of the manufacturer in combination with RiboLock™ ribonuclease inhibitor (Fermentas GmbH, St. Leon-Rot, Germany). Due to the large size of the Api m 5 cDNA, two different primers were used for reverse transcription of Api m 5 mRNA in the total RNA sample. A oligodT-20 primer (SEQ ID NO:9) was used for full length transcription and the F2 back primer (see also Table 4) was used for enhanced transcription of the 5'-region of the mRNA of the gene. For this 5 µl of total bee RNA was mixed with 2 µl (2 pmol) oligonucleotide primer and 4 µl DEPC water. The reaction mix was incubated at 70° C. for 5 minutes to break secondary structures. After this, the reaction was chilled on ice. Subsequently, 1.5 µl DEPC water, 4 µl 5× reaction buffer, 2 µl dNTP mix (10 mM), and 0.5 µl ribonuclease inhibitor were added. The reaction mix was incubated at 37° C. for 5 minutes. Then 1 µl Reverse Transcriptase was added and the reaction was incubated at 50° C. for 60 minutes. After this the reaction was stopped by heating to 70° C. for 10 minutes and chilled on ice.

5.3 RT-PCR

First strand cDNA from bee venom gland tissue was used as template for PCR amplification of Api m 5 DNA sequences.

The sequence obtained through gene prediction was used to design the specific primers for Api m 5. These primers have been designed to allow subcloning into pIB/mel opt-H10 (Ref 42) The nucleotide sequences of the oligonucleotides are given in Table 4.

The PCR reactions contained 40.5 µl DEPC water, 5 µl 10× complete PCR buffer, 1 µl forward primer (100 pmol), 1 µl backward primer (100 pmol), 1 µl dNTP mix (10 mM), 0.5 µl bee venom gland tissue cDNA, and 1 µl Accuprime™ Taq polymerase (Invitrogen GmbH, Karlsruhe, Germany), to give a total reaction volume of 50 µl.

The PCR annealing temperatures varied according to the hybridisation temperatures (Tm) of the primers to the target sequences. The basic PCR temperature cycling program conditions were:

Step 1: 96° C., 1 minute
Step 2: 95° C., 30 seconds
Step 3: 50-57° C.*, 60 seconds
Step 4: 72° C., 90 seconds
Repeat steps 2-4×29 times
Step 5: 72° C., 10 minutes
Step 6: 4° C., until end
*(depending on the Tm of the primer.)

Part of the PCR reaction was run on a 1% agarose (peqGOLD universal agarose, peqlab GmbH, Erlangen, Germany) gel in 0.5×TAE (20 mM Tris, 10 mM acetic acid, 0.5 mM EDTA, pH 8.5) buffer and amplified DNA products visualised with ethidium bromide and UV illumination.

First attempts to amplify the gene with F1 for GNOMON primer and F3 back primer failed. The gene was therefore divided into three approximately equal sized fragments and it was tried to amplify these parts separately. The fragment F3, representing the 3'-region of the gene, was successfully amplified using primers "F3 for hyb" (SEQ ID NO:11) and "F3 back" (SEQ ID NO:10) from the oligodT-primed cDNA library. The middle part F2 was successfully amplified using primers "F2 for" (SEQ ID NO:13) and "F2 back" (SEQ ID NO:12) from oligodT- and "F2 back"-primed libraries. The amplification of the 5'-region, represented by fragment F1 failed with primers "F1 for GNOMON" (SEQ ID NO:15) and "F1 back" (SEQ ID NO:14) from either oligodT- or "F2 back"-primed cDNA. However, after revealing the alternative gene prediction by GeneMark and therefore altering the sequence published in the nucleic database for the putative gene, amplification with primers "F1 for GeneMark" (SEQ ID NO:16) and "F1 back" (SEQ ID NO:14) was successful. The fragments were isolated by agarose gel electrophoresis and extraction from the gel slices was done with Gel extraction kit (Qiagen GmbH, Hilden, Germany) according to the instructions of the manufacturer. Now the gene was present in three separate fragments (see also FIG. 4).

5.4 Subcloning and Sequencing

DNA from the PCR reaction was isolated using the QIAEX II gel extraction kit (Qiagen GmbH, Hilden, Germany). Subcloning for sequencing was done using a pUC-TA cloning strategy based on a derivative of pUC19 cut with the Xcm I restriction enzyme (New England Biolabs GmbH, Frankfurt am Main, Germany) (Ref. 43). The ligated DNA was transformed into *E. coli* of the strain TB1 by electroporation (1 mm cuvettes, EasyJect+, Hybaid, Heidelberg, Germany) and selected on ampicillin agar plates. DNA from selected clones was purified using the E.Z.N.A. Plasmid Purification Kit II from peqLab GmbH (Erlangen, Germany). The sequencing reaction was done with BigDye® Terminator Cycle Sequencing Kit from ABI (Applied Biosystems Applera Deutschland GmbH, Darmstadt, Germany) according to the manual. 25 cycles were run with a 30 seconds denaturation step at 96° C., 15 seconds annealing step at 50° C., and 4 minutes elongation step at 57° C. Sequencing primer were: "M13/Uni for" (SEQ ID NO:19) and "M13/Uni back" (SEQ ID NO:20) for pUC-vectors or "OpIE2 for" (SEQ ID NO:21) and "OpIE2 back" (SEQ ID NO:22) for pIB derived vectors. The analysis of the sequencing reaction was done on an ABI Prism 377 Genetic Analyser instrument.

5.5 Construction of Full Length Api m 5

The three fragments derived from RT-PCR were joined by hybridisation and cloning. Firstly the fragments F1 and F2 were hybridised in PCR reaction mix and subsequently amplified with "F1 for pIBXba" (SEQ ID NO:17) and "F2 back pIBNot" (SEQ ID NO:18). The resulting amplicon F1-2 was isolated from agarose gel, digested with Xba I and Not I restriction enzymes (Fermentas GmbH, St. Leon-Rot, Germany), again purified and ligated into pIB/mel opt-H 10 insect cell expression vector (Ref. 42) cut with the same enzymes and using T4 DNA ligase (Fermentas GmbH, St. Leon-Rot, Germany). The ligated DNA vector was transformed into E. coli of the strain TB1 by electroporation (1 mm cuvettes, EasyJect+, Hybaid, Heidelberg, Germany) and selected on ampicillin agar plates. Secondly the fragments F2 and F3 were hybridised in PCR reaction mix and subsequently amplified with "F2 for" (SEQ ID NO:13) and "F3 back" (SEQ ID NO:10). The resulting amplicon F2-3 was isolated from agarose gel, digested with Ssp I and Sac II (Cfr42 I) restriction enzymes (Fermentas GmbH, St. Leon-Rot, Germany), again purified and ligated into the above described vector carrying the F1-2 insert cut with the same enzymes and using T4 DNA ligase (Fermentas GmbH, St. Leon-Rot, Germany). The resulting vector pIB/Api5 contained the full length Api m 5 gene, except for the signal sequence which was replaced by the Melittin signal sequence for secretion and an N-terminal His-tag for simplified purification (see also FIG. 3). The full length sequence comprises 2328 base pairs (FIG. 6) coding for a 776 amino acid protein (FIG. 7).

Example 6

Expression and Purification of Recombinant Api m 5

High Five insect cells (Invitrogen GmbH, Karlsruhe, Germany) were used for expression. DNA was purified from bacterial cultures using the E.Z.N.A Plasmid Miniprep Kit II (peqLab GmbH, Erlangen, Germany). For transfection of purified DNA into cells, the reagent Cellfectin (Invitrogen GmbH, Karlsruhe, Germany) was used according to the manual of the manufacturer. Insect cells were grown in serum-free medium (Express Five SFM, containing 16.5 mmol/L glutamine and 10 mg/mL gentamycin; Invitrogen GmbH, Karlsruhe, Germany). Cells were selected for stable integration of the recombinant product by addition of 80 µg/mL Blasticidin S (Invitrogen GmbH, Karlsruhe, Germany) antibiotic to the medium. Medium of confluent transient or stably transfected insect cell expression cultures was collected. The supernatant was adjusted to pH 7.8 and centrifuged at 4000×g for 5 minutes. Aliquots of 5 to 100 mL medium were applied to a nickel-chelating affinity matrix (nitrilo-triacetic acid [NTA]-agarose, Qiagen GmbH, Hilden, Germany). The column was washed with 10 mL NTA binding buffer (50 mmol/L sodium phosphate, pH 7.6, 500 mmol/L NaCl) and pre-eluted with NTA-binding buffer containing 20 mmol/L imidazole. The recombinant protein was eluted from the matrix with 10 mL NTA-binding buffer containing 400 mmol/L imidazole. Purification was confirmed by SDS-PAGE and silver staining (see also FIG. 8).

Example 7

Enzymatic Activity of Recombinant Api m 5

Figure 10:
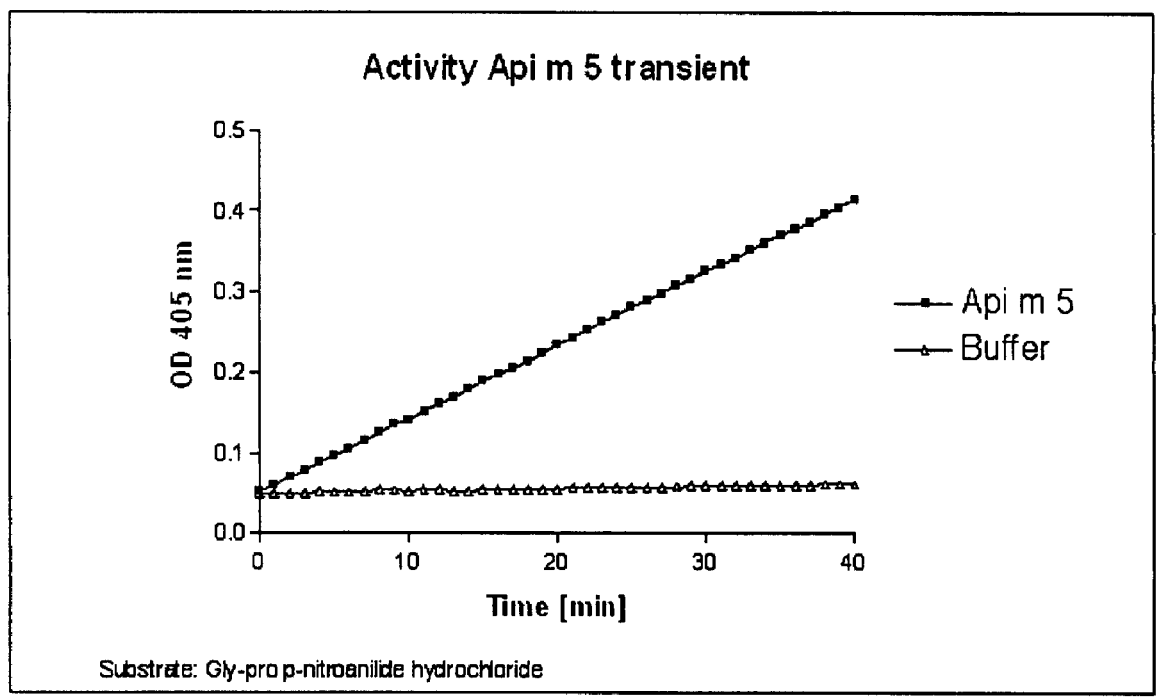
FIG. 10 shows the activity assay of purified recombinant Api m 5. the dipeptide substrate Gly-Pro p-nitroanilide hydrochloride was used to examine the dipeptidase activity of the purified recombinant protein. Clearly the peptidase activity of recombinant Api m 5 in releasing the chromogenic label from the dipeptide can be seen in comparison to buffer alone.

Analysis of the Api m 5 sequence revealed motives for a dipeptidylpeptidase activity (FIG. 10). One putative target of the enzyme might be the specific cleavage of the N-terminal peptide of pro-melittin to generate active melittin. The cleavage releases dipeptides with a C-terminal proline. Activity of such dipeptidases can be examined using the substrate Gly-Pro p-nitroanilide hydrochloride (Ref 22). Purified Api m 5 in NTA-binding buffer containing 300 mmol/L was incubated with 0.5 mM glycylpropyl p-nitroanilide (Gly-Pro-pNA, Sigma-Aldrich GmbH, Munich, Germany) as a substrate at 25° C. Released p-nitroaniline was spectrophotometrically monitored at 405 nm (FIG. 10).

REFERENCES

1. Obispo, T. Nuevos conceptos en la fabricación de extractos de veneno de himenópteros. Alergol Immunol Clin 17, 215-220 (2002)
2. Helbling, A., Hurni, T., Mueller, U. R., Pichler, W. J. Incidence of anaphylaxis with circulatory symptoms: a study over a 3-year period comprising 940,000 inhabitants of the Swiss Canton Bern. Clin Exp Allergy 34, 285-90 (2004)
3. Eich-Wanger, C., Muller, U. R. Bee sting allergy in beekeepers. Clin Exp Allergy 28, 1292-8 (1998)
4. Dotimas, E. M., Hider, R. C. Honeybee Venom. Bee World 68, 51-70 (1987)
5. Skenderov, Ivanov. Bienenprodukte (Zemizdat Verlag, Sofia, 1983).
6. Habermann, E. Bienen-und Wespenstiche aus medizinischer Sicht. Allgemeine Deutsche Imkerzeitung 11, 301-304 (1974)
7. Kulike, H. Zur Struktur und Funktionsweise des Hymenopterenstachels. Amts-und Mitteilungsblatt der Bundesanstalt für Materialprüfung 16, 519-550 (1986)
8. Sobotka, A., Franklin, R., Valentine, M., Adkinson, N. F., Lichtenstein, L. M. Honey bee venom: Phospholipase A as the major allergen. J Clin Allergy Clin Immunol 53, 103 (1974)
9. Sobotka, A. K., Franklin, R. M., Adkinson, N. F., Jr., Valentine, M., Baer, H., Lichtenstein, L. M. Allergy to insect stings. II. Phospholipase A: the major allergen in honeybee venom. J Allergy Clin Immunol 57, 29-40 (1976)
10. Hoffman, D. R., Shipman, W. H. Allergens in bee venom. I. Separation and identification of the major allergens. J Allergy Clin Immunol 58, 551-62 (1976)
11. Kuchler, K., Gmachl, M., Sippl, M. J., Kreil, G. Analysis of the cDNA for phospholipase A2 from honeybee venom glands. The deduced amino acid sequence reveals homology to the corresponding vertebrate enzymes. Eur J Biochem 184, 249-54 (1989)
12. Gmachl, M., Kreil, G. Bee venom hyaluronidase is homologous to a membrane protein of mammalian sperm. Proc Natl Acad Sci USA 90, 3569-73 (1993)
13. Vlasak, R., Unger-Ullmann, C., Kreil, G., Frischauf, A. M. Nucleotide sequence of cloned cDNA coding for honeybee prepromelittin. Eur J Biochem 135, 123-6 (1983)
14. Hoffman, D. R., Shipman, W. H., Babin, D. Allergens in bee venom II. Two new high molecular weight allergenic specificities. J Allergy Clin Immunol 59, 147-53 (1977)
15. Kettner, A., Hughes, G. J., Frutiger, S., Astori, M., Roggero, M., Spertini, F., Corradin, G. Api m 6: a new bee venom allergen. J Allergy Clin Immunol 107, 914-20 (2001)
16. Wood, C. L., Hoffman, D. R. Two-dimensional polyacrylamide gel electrophoresis of *hymenoptera* venom and venom sac extracts. Toxicon 21, 291-9 (1983)
17. Kettner, A., Henry, H., Hughes, G. J., Corradin, G., Spertini, F. IgE and T-cell responses to high-molecular weight allergens from bee venom. Clin Exp Allergy 29, 394-401 (1999)
18. Hoffman, D. R. in Advances in Experimental Medicine and Biology (eds. Singh, B. R., Thu, A. T.) 169-186 (Plenum Press, New York and London, 1996).
19. Wypych, J. I., Abeyounis, C. J., Reisman, R. E. Analysis of differing patterns of cross-reactivity of honeybee and 19. yellow jacket venom-specific IgE: use of purified venom fractions. Int Arch Allergy Appl Immunol 89, 60-6 (1989)
20. Castro, F. F., Palma, M. S., Brochetto-Braga, M. R., Malaspina, O., Lazaretti, J., Baldo, M. A., Antila, M. A., Zuppi, L. J., Croce, J., Cossermelli, W. Biochemical properties and study of antigenic cross-reactivity between Africanized honey bee and wasp venom. J Investig Allergol Clin Immunol 4, 37-41 (1994)
21. Hoffman, D. R., Dove, D. E., Moffitt, J. E., Stafford, C. T. Allergens in *Hymenoptera* venom. XXI. Cross-reactivity and multiple reactivity between fire ant venom and bee and wasp venoms. J Allergy Clin Immunol 82, 828-34 (1988)
22. Kumagai, Y., Konishi, K., Gomi, T., Yagishita, H., Yajima, A., Yoshikawa, M. Enzymatic properties of dipeptidyl aminopeptidase IV produced by the periodontal pathogen *Porphyromonas gingivalis* and its participation in virulence. Infect Immun 68, 716-24 (2000)
23. Dobers, J., Zimmermann-Kordmann, M., Leddermann, M., Schewe, T., Reutter, W., Fan, H. Expression, purification, and characterization of human dipeptidyl peptidase IV/CD26 in Sf9 insect cells. Protein Expr Purif 25, 527-32 (2002)
24. King, T. P. in Molecular approaches to the study of allergens (ed. Baldo, B. A.) viii, 166 p. (Karger, Basel; New York, 1990).
25. Muller, U. R. Recombinant *Hymenoptera* venom allergens. Allergy 57, 570-6 (2002)
26. Muller, U. R. New developments in the diagnosis and treatment of *Hymenoptera* venom allergy. Int Arch Allergy Immunol 124, 447-53 (2001)
27. Hemmer, W., Focke, M., Kolarich, D., Dalik, I., Gotz, M., Jarisch, R. Identification by immunoblot of venom glycoproteins displaying immunoglobulin E-binding N-glycans as cross-reactive allergens in honeybee and yellow jacket venom. Clin Exp Allergy 34, 460-9 (2004)
28. Tretter, V., Altmann, F., Kubelka, V., Marz, L., Becker, W. M. Fucose alpha 1,3-linked to the core region of glycoprotein N-glycans creates an important epitope for IgE from honeybee venom allergic individuals. Int Arch Allergy Immunol 102, 259-66 (1993)
29. Huby, R. D., Dearman, R. J., Kimber, I. Why are some proteins allergens? Toxicol Sci 55, 235-46 (2000)
30. Petersen, A., Mundt, C. Investigations on the carbohydrate moieties of glycoprotein allergens. J Chromatogr B Biomed Sci Appl 756, 141-50 (2001)
31. Jenkins, N., Parekh, R. B., James, D. C. Getting the glycosylation right: implications for the biotechnology industry. Nat Biotechnol 14, 975-81 (1996)
32. Elbein, A. D. The role of N-linked oligosaccharides in glycoprotein function. Trends Biotechnol 9, 346-52 (1991)
33. Sudowe, S., Montermann, E., Steitz, J., Tuting, T., Knop, J., Reske-Kunz, A. B. Efficacy of recombinant adenovirus as vector for allergen gene therapy in a mouse model of type I allergy. Gene Ther 9, 147-56 (2002)
34. Hunt, K. J., Valentine, M. D., Sobotka, A. K., Benton, A. W., Amodio, F. J., Lichtenstein, L. M. A controlled trial of immunotherapy in insect hypersensitivity. N Engl J Med 299, 157-61 (1978)
35. Schiavino, D., Nucera, E., Pollastrini, E., De Pasquale, T., Buonomo, A., Bartolozzi, F., Lombardo, C., Roncallo, C., Patriarca, G. Specific ultrarush desensitization in *Hymenoptera* venom-allergic patients. Ann Allergy Asthma Immunol 92, 409-13 (2004)
36. Hamilton, R. G. Diagnosis of *Hymenoptera* venom sensitivity. Curr Opin Allergy Clin Immunol 2, 347-51 (2002)
37. Poulsen, L. K. In vivo and in vitro techniques to determine the biological activity of food allergens. J Chromatogr B Biomed Sci Appl 756, 41-55 (2001)
38. Schmid-Grendelmeier, P., Crameri, R. Recombinant allergens for skin testing. Int Arch Allergy Immunol 125, 96-111 (2001)
39. Williams, L. W., Bock, S. A. Skin testing and food challenges in allergy and immunology practice. Clin Rev Allergy Immunol 17, 323-38 (1999)
40. Barbee, R. A., Lebowitz, M. D., Thompson, H. C., Burrows, B. Immediate skin-test reactivity in a general population sample. Ann Intern Med 84, 129-33 (1976)
41. Altschul, S. F., Gish, W., Miller, W., Myers, E. W., Lipman, D. J. Basic local alignment search tool. J Mol Biol 215, 403-10 (1990)
42. Grunwald, T., Bockisch, B., Spillner, E., Ring, J., Bredehorst, R., Ollert, M. W. Molecular cloning and expression in insect cells of honeybee venom allergen acid phosphatase (Api m 3). J Allergy Clin Immunol 117, 848-54 (2006)
43. Borovkov, A. Y., Rivkin, M. I. XcmI-containing vector for direct cloning of PCR products. Biotechniques 22, 812-4 (1997)

The invention claimed is:

1. A nucleic acid encoding a polypeptide capable of binding to IgE from subjects allergic to venom of an insect from the order *Hymenoptera*, wherein said polypeptide has the amino acid sequence of SEQ ID NO: 2.

2. The nucleic acid of claim 1; wherein the nucleic has the nucleotide sequence of SEQ ID NO: 1.

3. The nucleic acid of claim 1, wherein the insect is a bee from the genus *Apis*.

4. The nucleic acid of claim 3, wherein the bee is *Apis mellifera*.

5. An expression vector comprising the nucleic acid of claim 1 operationally linked to an expression control sequence.

6. The expression vector of claim 5, wherein the nucleic acid is linked in frame to a nucleic acid encoding an additional polypeptide.

7. The expression vector of claim 6, wherein the additional polypeptide is selected from the group comprising a poly-Histidine tag, glutathione-S-transferase, β-galactosidase, a cytokine, an IgG-Fc or another *Hymenoptera* venom protein or antigenic fragment thereof.

8. The expression vector of claim 5, wherein the vector is suitable for expression in bacterial or insect cells.

9. The expression vector of claim 5, wherein the vector is pIB/Api m 5.

10. A host cell comprising the expression vector of claim 5.

11. The host cell of claim 10, wherein the cell is an insect cell or a bacterial cell.

12. A method of producing a polypeptide encoded by the nucleic acid of claim 1 comprising culturing the host cell of claim 10 under appropriate conditions for expression of said polypeptide and purifying said polypeptide.

13. A pharmaceutical composition comprising the expression vector of claim 5.

14. The pharmaceutical composition of claim 13, further comprising a suitable adjuvant and/or expedient and/or further polypeptides from the venom of an insect from the order *Hymenoptera*.

15. A method of preparing a composition for diagnosing an allergy to venom of an insect from the order *Hymenoptera* comprising the step of performing the method of claim 12.

16. A method of preparing a composition for treating subjects allergic to the venom of an insect from the order *Hymenoptera*, comprising the step of performing the method of claim 12.

* * * * *